US010195287B2

(12) United States Patent
Barlos et al.

(10) Patent No.: US 10,195,287 B2
(45) Date of Patent: Feb. 5, 2019

(54) BIOLOGICALLY ACTIVE INSULIN DERIVATIVES

(71) Applicant: Chemical & Biopharmaceutical Laboratories of Patras S.A., Patras (GR)

(72) Inventors: Kleomenis Barlos, Patras (GR); Dimitrios Gatos, Patras (GR); Kostas Barlos, Patras (GR); Michail Ziovas, Patras (GR)

(73) Assignee: CHEMICAL & BIOPHARMACEUTICALS LABORATORIES OF PATRAS S.A., Patras (GR)

( * ) Notice: Subject to any disclaimer, the term of this patent is extended or adjusted under 35 U.S.C. 154(b) by 0 days.

(21) Appl. No.: 15/101,597

(22) PCT Filed: Dec. 4, 2014

(86) PCT No.: PCT/IB2014/066588
§ 371 (c)(1),
(2) Date: Jun. 3, 2016

(87) PCT Pub. No.: WO2015/083114
PCT Pub. Date: Jun. 11, 2015

(65) Prior Publication Data
US 2016/0375146 A1 Dec. 29, 2016

(30) Foreign Application Priority Data

Dec. 5, 2013 (GB) .................................. 1321489.5

(51) Int. Cl.
A61K 38/28 (2006.01)
A61K 47/65 (2017.01)
C07K 14/62 (2006.01)

(52) U.S. Cl.
CPC .............. A61K 47/65 (2017.08); A61K 38/28 (2013.01); C07K 14/62 (2013.01)

(58) Field of Classification Search
CPC .................................................... A61K 38/28
See application file for complete search history.

(56) References Cited

U.S. PATENT DOCUMENTS

| 3,847,893 | A | 11/1974 | Brandenburg et al. | |
|---|---|---|---|---|
| 5,597,796 | A | 1/1997 | Brange | |
| 8,192,957 | B2 | 6/2012 | Weiss | |
| 2007/0129284 | A1* | 6/2007 | Kjeldsen | C07K 14/62 435/69.1 |
| 2009/0036353 | A1* | 2/2009 | Behrens | B82Y 5/00 514/1.1 |
| 2009/0069216 | A1 | 3/2009 | Naver et al. | |
| 2010/0216690 | A1 | 8/2010 | Madsen et al. | |

FOREIGN PATENT DOCUMENTS

| EP | 0 427 296 A1 | 5/1991 |
|---|---|---|
| EP | 0 741 188 A2 | 11/1996 |
| EP | 1 193 272 A1 | 4/2002 |
| WO | 1995/016708 A1 | 6/1995 |
| WO | 1999/064574 A1 | 12/1999 |
| WO | 2005/054291 A1 | 6/2005 |
| WO | 2007/096332 A1 | 8/2007 |
| WO | 2007/104738 A2 | 9/2007 |
| WO | 2009022005 A1 | 2/2009 |
| WO | 2011031662 A1 | 3/2011 |
| WO | 2011159895 A2 | 12/2011 |
| WO | 2015083114 A2 | 6/2015 |

OTHER PUBLICATIONS

Brandenburg et al., "The Effect of a Non-Peptide Interchain Crosslink on the Reoxidation of Reduced Insulin," Hoppe-Seyler's Z. Physiol. Chem., 1973, Bd. 354, S. 613-627.
Brems et al., "The Conformational Stability and Flexibility of Insulin with an Additional Intramolecular Cross-link," The Journal of Biological Chemistry, 1991, 266:3:16-11-1615.
Busse et al., "Synthesis and Properties of Corbonylbis(methionyl)insulin, a Proinsulin Analogue Which is Convertible to Insulin by Cyanogen Bromide Cleavage," Biochemistry, 1976, 15:8:1649-1657.
Cutfield et al., "Evidence Concerning Insulin Activity from the Structure of a Cross-Linked Derivative," Hoppe-Seyler's Z. Physiol. Chem., 1981, Bd. 362, S. 755-761.
Geiger et al., "Bis(tert.-butyloxycarbonyl)insulin," Hoppe-Seyler's Z. Physiol. Chem., 1971, Bd. 352, S. 1487-1490.
Geiger et al., "Insulin Synthesis From Natural Chains bby Means of Reversible Bridging Compounds," Biochemical and Biophysical Research Communications, 1973, 55:1:60-66.
Huang et al, "The relationship between the connecting peptide of recombined single chain insulin and its biological function," Science in China (Series C), 2001, 44:6:593-600.
International Search Report corresponding to International Patent Application No. PCT/IB2014/066588, dated Aug. 19, 2015.
Lindsay, "Intramolecular Cross-Linked Insulin," FEBS Letters, 1971, 21:1:105-108.
Written Opinion of the International Searching Authority corresponding to International Patent Application No. PCT/IB2014/066588, dated Aug. 19, 2015.
Berge et al. (1977) "Pharmaceutical Salts," J. Pharm. Sci. 66(1):1-19.

(Continued)

Primary Examiner — Gyan Chandra
(74) Attorney, Agent, or Firm — Brian C. Trinque; Benjamin Vaughan; Lathrop Gage LLP

(57) ABSTRACT

A first aspect of the invention relates to a single chain insulin analog comprising: (A) the A-chain of human or animal insulin, or an analog or derivative thereof; (B) the B-chain of human or animal insulin, or an analog or derivative thereof; (C) one or more disulfide bonds between said A-chain and said B-chain; and (D) a further covalent link, L, between a functional group of an amino acid in the A-chain and a functional group of an amino acid in the B-chain, at least one of said functional groups being an amino acid side chain functional group. Further aspects of the invention relate to pharmaceutical compositions comprising said single chain insulin derivatives, and therapeutic uses thereof.

21 Claims, No Drawings

(56) References Cited

OTHER PUBLICATIONS

Geiger et al. (1980) "[Insulin analogues with substitution of A1-glycine by D-amino acids and omega-amino acids (authors transl)]," Hoppe-Seyler's Zeitschrift fur Physiologische Chemie. 361(4):563-570.—English Abstract and Drawings only.
Horwell (1995) "The 'peptoid' approach to the design of non-peptide, small molecular agonists and antagonists of neuropeptides," Trends in Biotechnology.13(4):132-134.
Simon et al. (1992) "Peptoids: A modular approach to drug discovery," Proc. Natl. Acad. Sci. USA. 89(20):9367-9371.
Wang et al. (1991) "Insulin Analogues with modifications in the β-Turn of the B-Chain," Journal of Protein Chemistry. 10(3)313-324.

* cited by examiner

BIOLOGICALLY ACTIVE INSULIN DERIVATIVES

RELATED APPLICATIONS

This application is a 35 U.S.C. § 371 filing of International Application No. PCT/IB2014/066588, filed Dec. 4, 2014, which claims priority to Great Britain Patent Application No. 1321489.5, filed Dec. 5, 2013, the contents of which are incorporated herein by reference in their entirety for all purposes.

The present invention relates to insulin analogues having therapeutic applications in the treatment of diabetes. More specifically, but not exclusively, the invention relates to single chain insulin analogues comprising the A-chain and the B-chain of insulin, where in addition to intermolecular disulfide bonds, the chains are connected together through the functional group of an amino acid side chain of an amino acid in the A or the B-chain.

BACKGROUND TO THE INVENTION

Insulin is a peptide hormone secreted by the β-cells of the pancreas. It consists of two peptide chains, A and B, which are linked by two intermolecular disulphide bonds. The A-chain also contains an additional intramolecular disulfide bond. Human insulin has the structure 2.

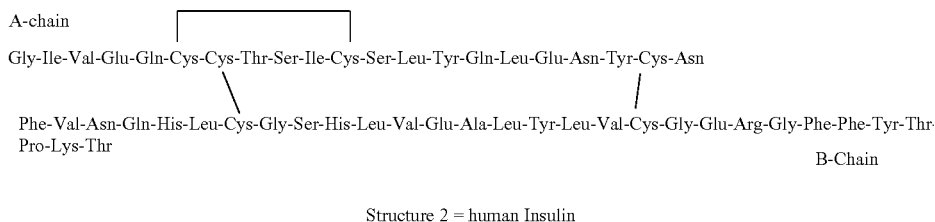

Structure 2 = human Insulin

Insulin is produced as a single-chain precursor, preproinsulin, which consists of a propeptide of 24 amino acid followed by proinsulin containing 86 amino acids. The sequence of the prepropeptide is Prepeptide-[B-chain]-Arg-Arg-[connecting peptide]-Lys-Arg-[A-chain], wherein the connecting peptide consists of 31 amino acids. After the enzymatic removal of the prepeptide, the three disulfide bonds are formed and proinsulin is produced.

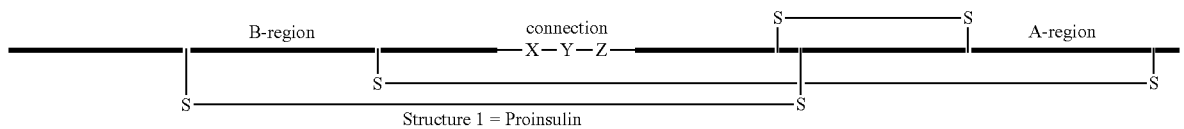

Structure 1 = Proinsulin

The mature insulin is then liberated by enzymatic cleavage of the connecting peptide at the Arg-Arg and Lys-Arg sites.

Proinsulin has a 100-fold lower affinity for the insulin receptor than native insulin because the essential residues for binding to the receptor, namely the N-terminal amino function of the A-chain and the C-terminal carboxyl function of the B-chain, are blocked.

The stability and solubility properties of insulin are important in the context of insulin therapeutics. A number of insulin analogues are known in the art.

By way of example, single-chain insulin analogues with insulin activity are disclosed in EP1193272. These single-chain insulins have a modified C-peptide of 5-18 amino acids and are reported to have up to 42% insulin activity.

U.S. Pat. No. 5,597,796 discloses insulin analogues in which two or more amino acid residues are substituted by Glu and/or Asp. Similarly, US 20090069216 and WO 2007/096332 disclose fast acting single chain insulins containing a modified B-chain and a connecting peptide. The resulting analogues are particularly well suited for transdermal administration. Fibrillation-resistant insulin and insulin analogues are disclosed in U.S. Pat. No. 8,192,957. Pegylated single chain insulins are disclosed in US 2010/0216690, whereas acylated single chain insulins are disclosed in WO 2007/104738.

WO 2005/054291 discloses single chain insulin analogues wherein the A-chain and B-chains are connected by a connecting peptide of 5-11 amino acids. Likewise, WO 95/16708 also discloses single chain insulin analogues wherein the A-chain and B-chains are connected by a connecting peptide of 1-15 amino acids, in which the C-terminal amino acid residue is other than Lys or Arg. EP0427296 discloses human insulin precursors of the general formula B(1-29)-$X_n$—Y-A(1-21), wherein $X_n$ is a peptide chain with n naturally occurring amino acid residues. Similarly, EP0741188 discloses single chain insulin derivatives of the formula b-BP-a having significant insulin activity; these single chain insulins are reported to have insulin activity but also a high affinity to the IGF-1 receptor.

Insulin derivatives containing D-amino acids at their A1 position have been shown to retain their biological activity [Geiger R, Geisen K, Regitz G, Summ H D, Langner D., Hoppe Seylers Z Physiol Chem. 1980 April; 361(4):563-70]. Insulin derivatives containing D-Glu at the B21 position have been shown to be equipotent with natural insulin [Wang S H, Hu S Q, Burke G T, Katsoyannis P G. J Protein Chem. 1991 June; 10(3):313-24.] The present invention seeks to provide new single chain insulin analogues that exhibit useful therapeutic properties, wherein the two insulin chains are connected through the amino acid side chain of at least one amino acid in the insulin A-chain or the B-chain.

STATEMENT OF INVENTION

A first aspect of the invention relates to a single chain insulin analogue comprising:

(A) the A-chain of human or animal insulin, or an analogue or derivative thereof;
(B) the B-chain of human or animal insulin, or an analogue or derivative thereof;
(C) one or more disulfide bonds between said A-chain and said B-chain; and
(D) a further covalent link, L, between a functional group of an amino acid in the A-chain and a functional group of an amino acid in the B-chain, at least one of said functional groups being an amino acid side chain functional group.

The presently claimed insulin analogues differ from those known in the art by virtue of the fact that the two insulin chains are linked via the functional group of at least one side chain of an amino acid already forming part of the insulin A-chain or B-chain. In view of this, they are distinct from conventional single chain peptides and cannot be considered as "proinsulin-like" peptides.

Proinsulin-like peptides, many of which are described in the literature and known in nature, contain a conventional connecting peptide, for example, where the N-terminal amino acid of one of the insulin chains is linked to the C-terminal amino acid of the other. Such peptides can be produced by conventional recombinant DNA techniques. However, is impossible to produce the presently claimed insulin analogues by recombinant DNA methodology or other biological methods. Accordingly, the insulin analogues described herein are the prototypes of a new single chain group of insulins not previously known in the art.

Incorporating a link between a functional group of an amino acid of one chain and the side chain functional group of an amino acid of the other chain means that at least one of the essential groups for biological activity, namely the N-terminal amino function of the A-chain or the C-terminal carboxyl function of the B-chain, remains free. Advantageously, incorporating an additional link between the A-chain and the B-chain decreases the flexibility of the chains, which in turn reduces fibrillation and precipitation and increases the chemical and enzymatic stability. Single chain insulins where the A and B chains are connected through a C-peptide often exhibit higher chemical stability, but tend to show lower affinity to the insulin receptor because the N-terminal amino function of the A-chain and C-terminal carboxyl function of the B-chain are blocked. The presently claimed single chain insulin analogues retain the advantages of an additional link between the chains to decrease flexibility, whilst at the same time alleviating the problem of low affinity by freeing up one or both of the terminal groups that are essential for activity.

DETAILED DESCRIPTION

The single-chain insulin analogues described herein encompass a group of structurally-related proteins wherein the A and B chains are covalently linked through at least one side chain functional group of an amino acid contained in the A- or the B-chain.

Thus, in a preferred embodiment, the present invention relates to single-chain insulin analogues comprising the A and B-chains of human or animal insulin, or analogues thereof, which are connected together, besides intermolecular disulfide bonds, by an additional linker which is formed between a functional group of an amino acid of the A-chain and a functional group of an amino acid of the B-chain, wherein at least one of these functional groups is on the side chain of an amino acid.

As used herein, the term "insulin analogue" refers to an altered form of insulin, different from any occurring in nature, but still available to the human body for performing the same action as human insulin in terms of glycemic control. Through genetic engineering of the underlying DNA, the amino acid sequence of insulin can be changed to alter its absorption, distribution, metabolism, and excretion characteristics. Officially, the U.S. Food and Drug Administration (FDA) refers to these as "insulin receptor ligands", although they are more commonly referred to as insulin analogues. Modifications include insulin analogues that are more readily absorbed from the injection site and therefore act faster than natural insulin injected subcutaneously, intended to supply the bolus level of insulin needed at mealtime (prandial insulin); and those that are released slowly over a period of between 8 and 24 hours, intended to supply the basal level of insulin during the day and particularly at nighttime (basal insulin). Fast acting insulin analogues include insulin lispro (Eli Lilly and Company) and insulin aspart (Novo Nordisk), whereas long acting insulin analogues include NPH insulin, insulin glulisine (Sanofi-Aventis), insulin detemir (Novo Nordisk) and insulin glargine (Sanofi-Aventis).

Insulin analogues include variants of insulin. As used herein, the term "variant" includes any variation wherein (a) one or more amino acid residues are replaced by a naturally or non-naturally occurring amino acid residue (b) the order of two or more amino acid residues is reversed, (c) both (a) and (b) are present together, (d) a spacer group is present between any two amino acid residues, (e) one or more amino acid residues are in peptoid form, (f) the (N—C—C) backbone of one or more amino acid residues of the peptide has been modified, or any of (a)-(f) in combination. Preferably, the variants arise from one of (a), (b) or (c).

More preferably, one or two amino acids residues are substituted by one or more other amino acid residues. Even more preferably, one amino acid residue is substituted by another amino acid residue. Preferably, the substitution is homologous.

Homologous substitution (substitution and replacement are both used herein to mean the interchange of an existing amino acid residue, with an alternative residue) may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine, diaminobutyric acid ornithine, norleucine ornithine, pyridylalanine, thienylalanine, naphthylalanine and phenylglycine, a more detailed list of which appears below. More than one amino acid residue may be modified at a time.

As used herein, amino acids are classified according to the following classes;
basic; H, K, R
acidic; D, E
non-polar; A, F, G, I, L, M, P, V, W
polar; C, N, Q, S, T, Y,
(using the internationally accepted single letter amino acid notation) and homologous and non-homologous substitution is defined using these classes. Thus, homologous substitution is used to refer to substitution from within the same class, whereas non-homologous substitution refers to substitution from a different class or by an unnatural amino acid.

Suitable spacer groups that may be inserted between any two amino acid residues of the carrier moiety include alkyl groups such as methyl, ethyl or propyl groups in addition to amino acid spacers such as glycine or β-alanine residues. A further form of variation, type (e), involving the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et PNAS (1992) 89(20), 9367-9371 and Horwell D C, Trends Biotechnol. (1995) 13(4), 132-134. Type (f) modification may occur by methods such as those described in International Application PCT/GB99/01855.

It is preferable for amino acid variation, preferably of type (a) or (b), to occur independently at any position. As mentioned above more than one homologous or non-homologous substitution may occur simultaneously. Further variation may occur by virtue of reversing the sequence of a number of amino acid residues within a sequence.

In one embodiment the replacement amino acid residue is selected from the residues of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

The replacement amino acid residue may additionally be selected from unnatural amino acids as described below.

As used herein, the term "derivative" refers to insulin that has undergone chemical modification, for example, to the amino acid side chains at the N-terminus and/or the C-terminus. Preferably, the chemical modification serves to alter the absorption, distribution, metabolism, and excretion characteristics of the analogue. Semisynthetic insulins were clinically used for some time based on chemical modification of animal insulins, for example Novo Nordisk enzymatically converted porcine insulin into semisynthetic 'human' insulin by removing the single amino acid that varies from the human variety, and chemically adding the human amino acid.

In one preferred embodiment, the insulin is chemically modified to alter its isoelectric point. Normal unmodified insulin is soluble at physiological pH. Modified derivatives of insulin have been created that have a shifted isoelectric point so that they exist in a solubility equilibrium in which most precipitates out but slowly dissolves in the bloodstream and is eventually excreted by the kidneys.

In one preferred embodiment, the single chain insulin analogue of the invention is derived from animal insulin.

The amino acid sequence of animal insulins in different mammals may be similar to human insulin (insulin human INN). However, there is considerable viability within vertebrate species. Porcine insulin has only a single amino acid variation from the human variety, and bovine insulin varies by three amino acids. Both are active on the human receptor with approximately the same strength. Bovine insulin and porcine insulin were the first clinically used insulin analogues (naturally occurring, produced by extraction from animal pancreas), at the time when biosynthetic human insulin (insulin human rDNA) was not available. Insulin from sharks and some species of fish may be also effective.

Preferably, the single chain insulin analogue of the invention comprises the A chain of animal insulin, or an analogue or derivative thereof.

Preferably, the single chain insulin analogue of the invention comprises the B chain of animal insulin, or an analogue or derivative thereof.

In another preferred embodiment, the single chain insulin analogue of the invention is derived from human insulin, or an analogue thereof. More preferably, the insulin is biosynthetic insulin (insulin human rDNA).

Preferably, the single chain insulin analogue of the invention comprises the A chain of human insulin, or an analogue or derivative thereof.

Preferably, the single chain insulin analogue of the invention comprises the B chain of human insulin, or an analogue or derivative thereof.

In one preferred embodiment, the covalent link, L, is between a functional group of an amino acid in said A-chain and a side chain functional group of an amino acid in the B-chain.

As used herein, the term "functional group" refers to specific groups of atoms or bonds within a molecule that are responsible for the characteristic chemical reactions of that molecule.

In another preferred embodiment, the covalent link, L, is between a side chain functional group of an amino acid in said A-chain and a side chain functional group of an amino acid in the B-chain.

In one preferred embodiment, the covalent link, L, is between the C-terminal amino acid of said A-chain and a side chain functional group of an amino acid in the B-chain.

In one preferred embodiment, the covalent link, L, is a direct bond.

In one preferred embodiment, the covalent link L is a direct bond between the side chain of an aspartic acid residue or of a glutamic acid residue at the C-terminal amino acid of the A-chain and the side chain amino function of a Lys residue in the B-chain.

In one preferred embodiment, the two insulin chains are linked directly through the functional groups of amino acids forming the respective insulin chains. For example, in one particularly preferred embodiment, the A and B-chains are connected by a link which in the simplest case is created between the functional group of at least one amino acid side chain of one of the insulin chains and the terminal amino acid of the other insulin chain. By way of example, in one preferred embodiment, the link is formed directly between the C-terminal amino acid of the A-chain and the side chain of an amino acid in the B-chain.

In one highly preferred embodiment, the two chains are connected directly through the side chain of an aspartic acid residue or of a glutamic acid residue contained as the C-terminal amino acid of the A-chain of insulin and the side chain amino function of the Lys residue contained as the C-terminal amino acid of B-chain of insulin.

In another embodiment of the invention, the two insulin chains are linked through a group, L, which itself can comprise individual parts X, Y, Z. For this particular embodiment, the groups X, Y and Z do not form part of the native A- or B-chains of insulin.

In one preferred embodiment, Group L may comprise one or more natural or unnatural amino acids, peptides (which may contain unnatural amino acid residues), or various peptide modifiers such as diacids, diamines, poly and oligoethylene glycols, thia-diacids, thia-amino acids, aminothiols etc. Components X, Y and Z are interchangeable in their sequence and optionally repeated.

More specifically, the linker group L contains at least one "modifier" in the form of a group X or a group Y. In addition, the linker group L may further comprise one or more conventional amino acid/peptide residues (Z).

As used herein, the term "modifier" refers to any group that is able to modify the biological and physicochemical properties of a peptide.

In one particularly preferred embodiment, the covalent linker, L, is a group comprising:

(i) at least one group X; and/or
(ii) at least one group Y; and/or
(iii) at least one group Z;
wherein:
X is a group of formula 1a or 1b
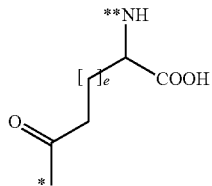
1a
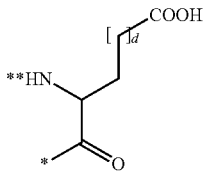
1b
wherein d and e are each independently an integer selected from 0 to 10, and * and ** denote the points of attachment to the respective adjacent groups;
Y is a group selected from the following:
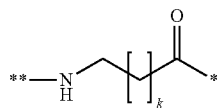
4
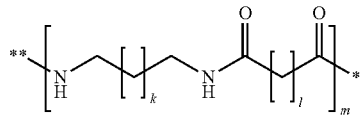
5
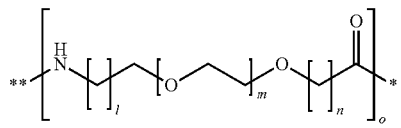
6
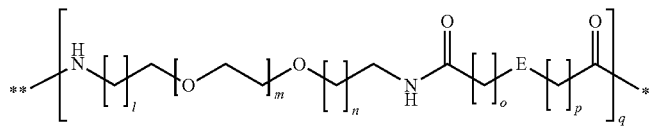
7
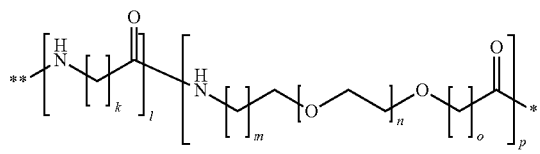
8
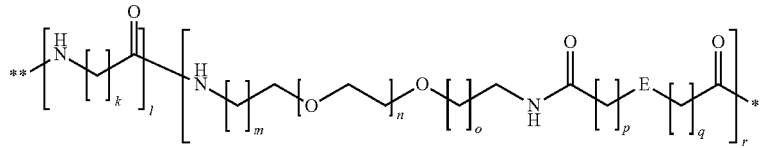
9
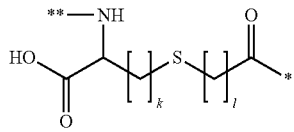
10
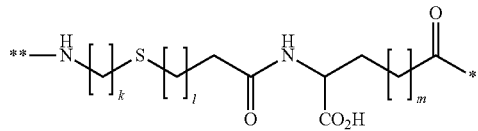
11

-continued

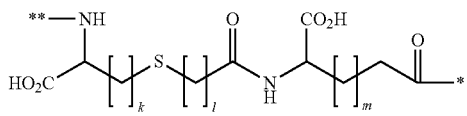
12

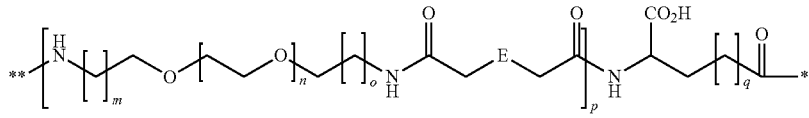
13

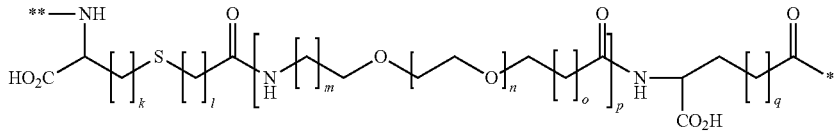
14

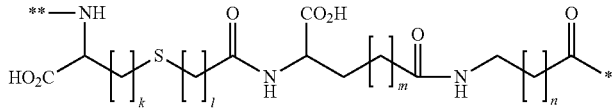
15

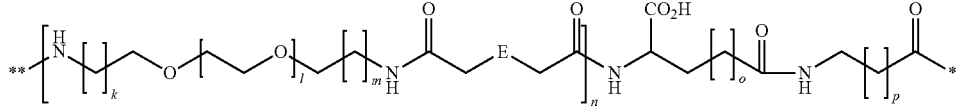
16

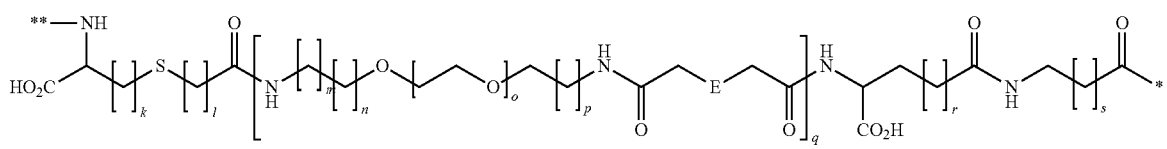
17

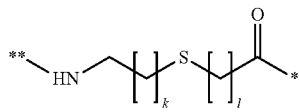
18 where * and ** denote the points of attachment to the respective adjacent groups;

k, l, m, n, o, p q, r, and s are each independently an integer selected from 0 to 18; and E is absent or is selected from $CH_2$, O, S and NR, where R is H, alkyl or aralkyl; and Z is a natural or unnatural amino acid.

As used herein, the term "alkyl" includes both saturated straight chain and branched alkyl groups which may be substituted (mono- or poly-) or unsubstituted. Preferably, the alkyl group is a $C_{1-20}$ alkyl group, more preferably a $C_{1-15}$, more preferably still a $C_{1-12}$ alkyl group, more preferably still, a $C_{1-6}$ alkyl group, more preferably a $C_{1-3}$ alkyl group. Particularly preferred alkyl groups include, for example, methyl, ethyl, propyl, isopropyl, butyl, isobutyl, tert-butyl, pentyl and hexyl. Suitable substituents include, for example, one or more groups selected from OH, O-alkyl, halogen, $NH_2$, NH-alkyl, N-(alkyl)$_2$, $CF_3$, $NO_2$, CN, COO-alkyl, COOH, $CONH_2$, CO—NH-alkyl, CO—N(alkyl)$_2$, $SO_2$-alkyl, $SO_2NH_2$ and $SO_2$—NH-alkyl.

As used herein, the term "aryl" refers to a $C_{6-12}$ aromatic group which may be substituted (mono- or poly-) or unsubstituted. Typical examples include phenyl and naphthyl etc. Suitable substituents include, for example, one or more groups selected from OH, O-alkyl, halogen, $NH_2$, NH-alkyl, N-(alkyl)$_2$, $CF_3$, $NO_2$, CN, COO-alkyl, COOH, $CONH_2$, CO—NH-alkyl, CO—N(alkyl)$_2$, $SO_2$-alkyl, $SO_2NH_2$ and $SO_2$—NH-alkyl.

The term "aralkyl" is used as a conjunction of the terms alkyl and aryl as given above.

Natural amino acids include alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

As used herein, the term "non-natural amino acid" or "unnatural amino acid" includes alpha and alpha-disubstituted amino acids, N-alkyl amino acids, lactic acid, halide derivatives of natural amino acids such as trifluorotyrosine, p-Cl-phenylalanine, p-F-phenylalanine, p-Br-phenylalanine, p-NO$_2$-phenylalanine, phenylglycine, sarcosine, penicillamine, D-2-methyltryptophan, phosphoserine, phosphothreonine, phosphotyrosine, p-I-phenylalanine, L-allyl-glycine, ß-alanine, ß-aspartic acid, ß-cyclohexylalanine, citrulline, homoserine, homocysteine, pyroglutamic acid, L-α-amino butyric acid, L-γ-amino butyric acid, L-α-amino isobutyric acid, α-cyclohexylglycine, diaminobutyric acid, diaminopimelic acid, N-ε-dinitrophenyl-lysine, L-1-naphthylalanine, L-2-naphthylalanine, 3-(2-pyridyl)-L-alanine, 3-(3-pyridyl)-L-alanine, 3-(4-pyridyl)-L-alanine, N-ε-methyl-lysine, N,N-ε-dimethyl-lysine, N,N,N-ε-trimethyl-lysine, 3-mercaptopropionic acid, L-ε-amino caproic acid, 7-amino heptanoic acid, 6-amino hexanoic acid L-methionine sulfone, ornithine, L-norleucine, L-norvaline, p-nitro-L-phenylalanine, L-hydroxyproline, γ-glutamic acid, γ-amino butyric acid L-thioproline, methyl derivatives of phenylalanine (Phe) such as 4-methyl-Phe, pentamethyl-Phe, L-Phe (4-amino), L-Tyr (methyl), L-Phe (4-isopropyl), L-Tic (1,2,3,4tetrahydroiso-quinoline-3-carboxyl acid), L-diaminopropionic acid and L-Phe (4-benzyl).

Advantageously, the introduction of unnatural amino acids leads to an increase in the enzymatic stability of the peptides.

The insulin analogues of the present invention may comprise amino acids in the L or D form, i.e. one or more residues, preferably all the residues may be in the L or D form. In one preferred embodiment, the linkage between the chains is formed between the C-terminal amino acid of the A-chain of human or animal insulin, or analogue or derivative thereof, and the side chain of the lysine residue in position 29 of the B-chain of human or animal insulin, or analogue or derivative thereof.

In one preferred embodiment, the linker group L is between a side chain carboxyl group of one amino diacid present in the C-terminal part of the A-chain and the side chain of an diaminoacid, preferably but not exclusively, positioned in the B29 position of the B-chain (see structure 3). As used herein the term "C-terminal part" refers to the last 10 amino acids of the A-chain including possible peptide extensions.

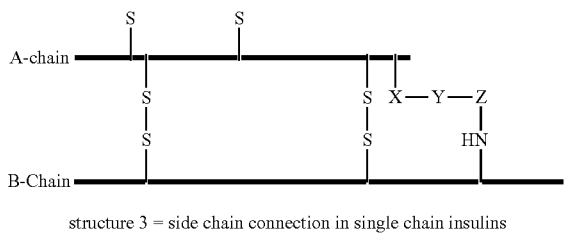

structure 3 = side chain connection in single chain insulins

The linker may be of any length so long as the linker provides the structural conformation necessary for the single-chain insulin analogue to have a glucose uptake and insulin receptor binding effect.

Incorporating the linker group L at the Lys(B29) side chain is particularly preferred. In one highly preferred embodiment, the linker comprises a lypophilic modifier, or comprises a modifier which combines lypophilic and hydrophylic properties.

In one preferred embodiment, the A-chain comprises amino acids 1 to 21 of human insulin counting from the N-terminal end of the A chain.

In one preferred embodiment, the A-chain consists of amino acids 1 to 21 of human insulin counting from the N-terminal end of the A chain.

In another preferred embodiment, the A-chain comprises amino acids 1 to 20 of human insulin counting from the N-terminal end of the A chain.

In another preferred embodiment, the A-chain consists of amino acids 1 to 20 of human insulin counting from the N-terminal end of the A chain.

In one preferred embodiment, the B-chain comprises amino acids 1 to 29 of human insulin counting from the N-terminal end of the A chain.

In one preferred embodiment, the B-chain consists of amino acids 1 to 29 of human insulin counting from the N-terminal end of the A chain.

In one preferred embodiment, the B-chain of insulin further comprises up to 20 additional natural or unnatural amino acids at the C-terminal end. Preferably, the B-chain further comprises from 1 to 10, or more preferably from 1 to 5 additional natural or unnatural amino acids at the C-terminal end. In one highly preferred embodiment, the B-chain further comprises 1, 2 or 3 additional natural or unnatural amino acids at the C-terminal end. More preferably still, the B-chain further comprises 1, 2 or 3 additional natural amino acids at the C-terminal end.

In one preferred embodiment, the single chain insulin analogue comprises one or more of:
(i) an intermolecular disulfide bond between the cysteine in position 7 of the insulin A-chain and the cysteine in position 7 of the insulin B-chain;
(ii) an intermolecular disulfide bond between the cysteine in position 20 of the insulin A-chain and the cysteine in position 19 of the insulin B-chain;
(iii) an intramolecular disulfide bond between the cysteine in position 6 and the cysteine in position 11 of the insulin A-chain.

In one preferred embodiment, the single chain insulin analogue comprises one of (i), (ii) and (ii) above.

In another preferred embodiment, the single chain insulin analogue comprises two of (i), (ii) and (ii) above.

In another preferred embodiment, the single chain insulin analogue comprises (i), (ii) and (ii) above.

In one preferred embodiment, the single chain insulin analogue is of formula (I), (I)

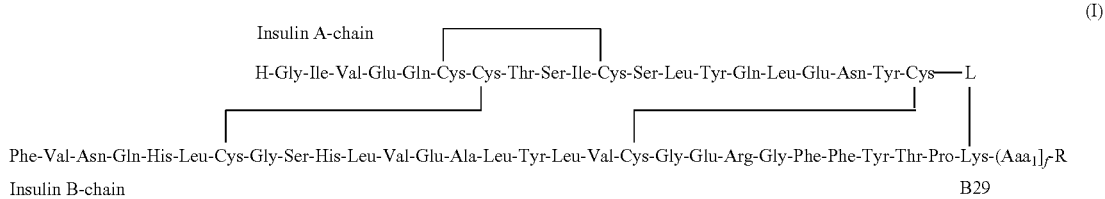

wherein:
L is as defined above;
each $Aaa_1$ is independently a natural or unnatural amino acid;
f is 0 to 20;
R is OH or $NH_2$.

In one preferred embodiment, R is OH, f is 0, 1, 2 or 3 and each $Aaa_1$ is independently a natural amino acid. More preferably, the natural amino acid is selected from Arg and Thr.

In one preferred embodiment, L is selected from the following groups:
(i) $—(X)_a(Y)_b—(Z)_c—$
(ii) $—(Y)_b—(X)_a—(Z)_c—$
(iii) $—(Y)_b—(Z)_c—(X)_a—$
(iv) $—(X)_a—(Z)_c—(Y)_b—$
(v) $—(Z)_c—(X)_a—(Y)_b—$
(vi) $—(Z)_c—(Y)_b—(X)_a—$
where a, b and c are each independently an integer selected from 0 to 5.

In one preferred embodiment, a, b and c are each independently 0, 1 or 2.

In one preferred embodiment, L is $—(X)_a—(Y)_b—(Z)_c—$ where a is 1, and b and c are both 0.

In another preferred embodiment, L is $—(X)_a—(Y)_b—(Z)_c—$ where a and b are 1, and c is 0.

In another preferred embodiment, L is $—(X)_a—(Y)_b—(Z)_c—$ where a is 1, b is 2, and c is 0.

In another preferred embodiment, L is $—(X)_a—(Y)_b—(Z)_c—$ where a is 1, b is 0, and c is 2.

In another preferred embodiment, L is $—(X)_a—(Y)_b—(Z)_c—$ where a is 0, b is 0, and c is 1 or 2.

In one preferred embodiment, L is a direct bond, i.e. a, b and c are all 0.

In one preferred embodiment, X is a group of formula 1a as defined above.

In one preferred embodiment, Y is a group of formula 6 as defined above.

In one preferred embodiment, Y is a group of formula 6a or 6b.

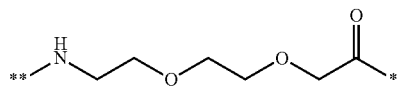

6a

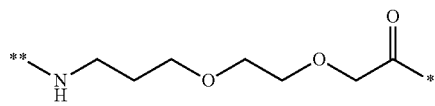

6b where * and ** denote the points of attachment to the respective adjacent groups.

In one preferred embodiment, Y is a group of formula 18 as defined above.

In one preferred embodiment, Y is a group of formula 18a, where I is 1, 2, 3, 4 or 5

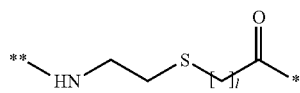

18a where * and ** denote the points of attachment to the respective adjacent groups.

In one preferred embodiment, the single chain insulin is selected from the following:

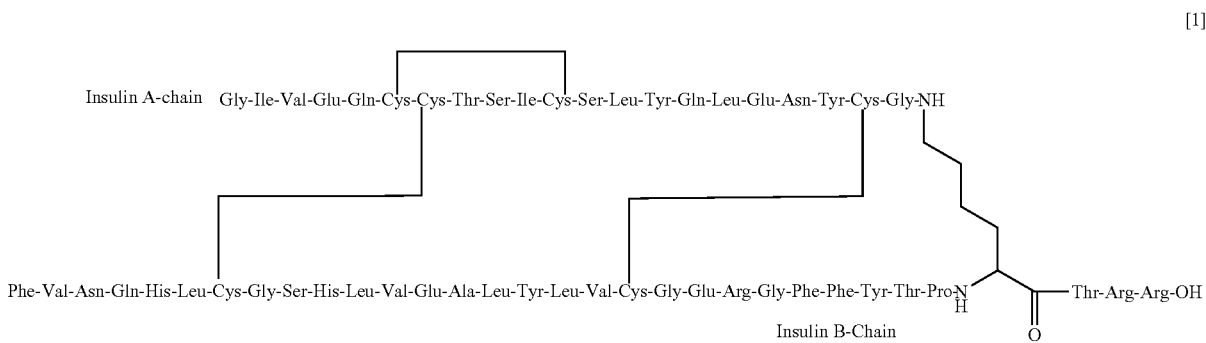

[1]

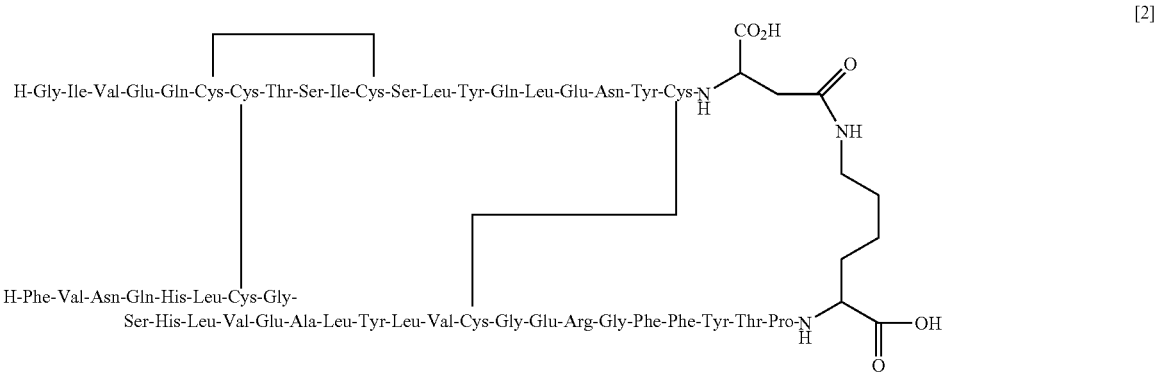

[2]

-continued

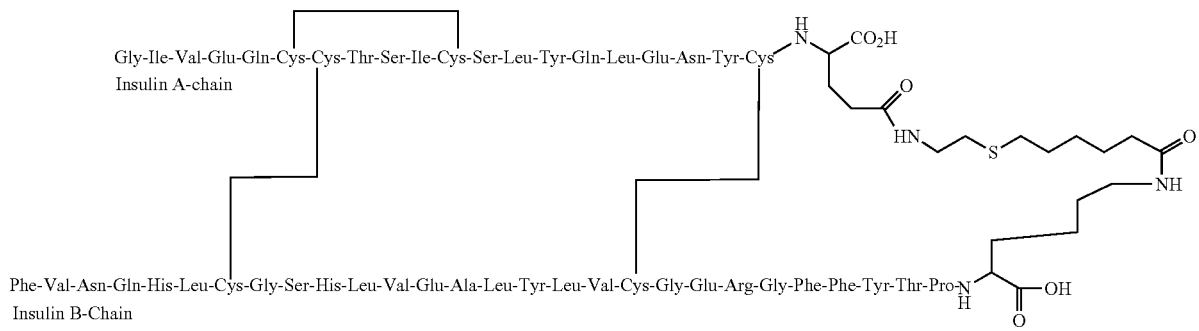

[3]

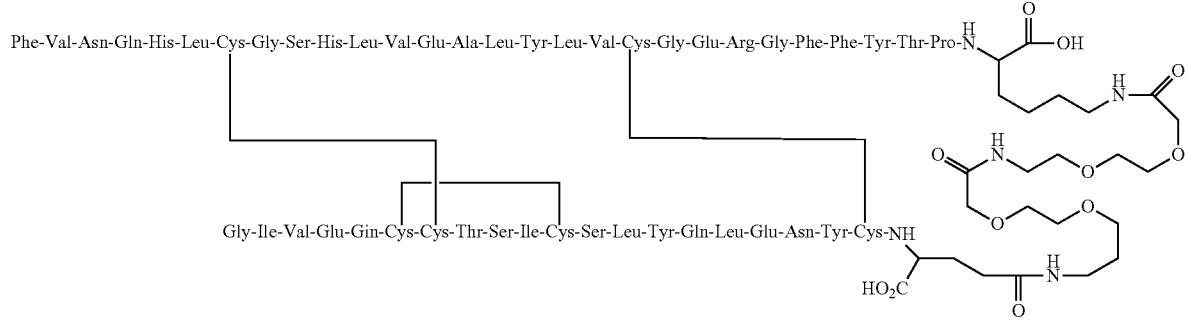

[4]

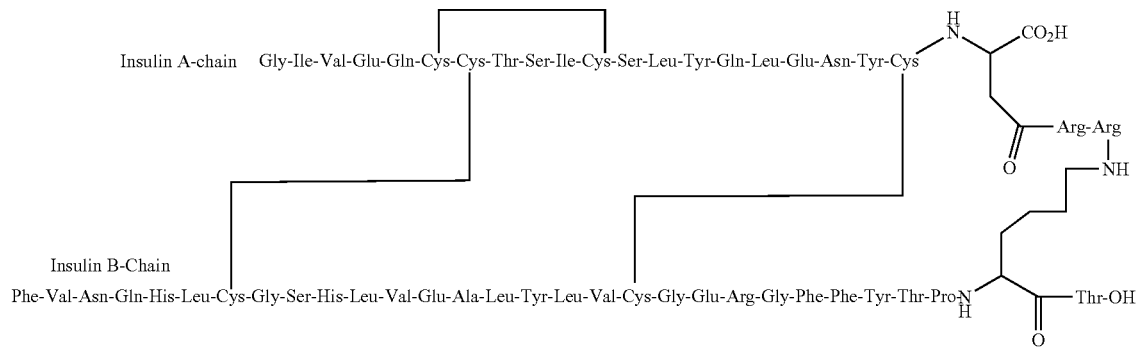

[5]

Pharmaceutical Compositions

One aspect of the invention relates to a pharmaceutical composition comprising an insulin analogue of the invention admixed with a pharmaceutically acceptable diluent, excipient or carrier, or a mixture thereof. Even though the analogues of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition.

Examples of preservatives include sodium benzoate, sorbic acid and esters of p-hydroxybenzoic acid. Antioxidants and suspending agents may be also used.

Salts/Esters

The insulin analogues of the present invention can be present as salts or esters, in particular pharmaceutically acceptable salts or esters.

Pharmaceutically acceptable salts of the analogues of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers and tautomers of the analogues of the invention. The man skilled in the art will recognise compounds that possess an optical properties (one or more chiral carbon atoms) or tautomeric characteristics. The corresponding enantiomers and/or tautomers may be isolated/prepared by methods known in the art.

Stereo and Geometric Isomers

Some of the analogues of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those analogues, and mixtures thereof. The terms used in the claims encompass these forms, provided said forms retain the appropriate functional activity (though not necessarily to the same degree).

The present invention also includes all suitable isotopic variations of the analogues or pharmaceutically acceptable salts thereof. An isotopic variation is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the analogues of the present invention and pharmaceutically acceptable salts thereof of this invention can generally be prepared by conventional procedures using appropriate isotopic variations of suitable reagents.

Solvates

The present invention also includes solvate forms of the analogues of the present invention. The terms used in the claims encompass these forms.

Polymorphs

The invention furthermore relates to analogues of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

The invention further includes analogues of the present invention in prodrug form. Such prodrugs are generally analogues of the invention wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Preferably, these compositions contain from 1 to 250 mg and more preferably from 10-100 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Depending upon the need, the agent may be administered at a dose of from 0.01 to 30 mg/kg body weight, such as from 0.1 to 10 mg/kg, more preferably from 0.1 to 1 mg/kg body weight.

In an exemplary embodiment, one or more doses of 10 to 150 mg/day will be administered to the patient.

Therapeutic Use

Another aspect of the invention relates to single chain insulin analogues as described above for use as a medicament.

Another aspect of the invention relates to single chain insulin analogues as described above for use in treating or preventing diabetes, or treating or preventing hyperglycemia.

Another aspect of the invention relates to single chain insulin analogues as described above in the preparation of a medicament for treating diabetes, or treating or preventing hyperglycemia.

As used herein the phrase "preparation of a medicament" includes the use of an analogue of the invention directly as the medicament in addition to its use in a screening programme for further therapeutic agents or in any stage of the manufacture of such a medicament.

Another aspect of the invention relates to a method of treating diabetes or treating or preventing hyperglycemia in a subject in need thereof, said method comprising administering a therapeutically effective amount of a single chain insulin analogue as described above.

The present invention is further described by way of the following non-limiting examples.

EXAMPLES

Abbreviations

Boc t-butyloxycarbonyl
CTC chlorotrityl chloride
NMP N-methylpyrrolidone
DCM dichoromethane
TFA trifluoroacetic acid
RE rotary evaporator
DEE diethyl ether
DIC N,N'-diisopropylcarbodiimide
HOBt hydroxybenzotriazole
HOSu N-hydroxysuccinimide
DMF dimethylformamide
EDAC 1-ethyl-3-(3-dimethylaminopropyl)carbodiimide
RT room temperature
DTT dithiothreitol
DMSO dimethylsulfoxide
MMt monomethoxytrityl
Trt trityl
DIPEA N,N-diisopropylethylamine
Fmoc fluorenylmethyloxycarbonyl
MeOH methanol
AcOH acetic acid
TFE trifluoroethyl alcohol
Dde N-(1-(4,4-dimethyl-2,6-dioxocyclohexylidene)ethyl)

Example 1

Synthesis of Single Chain Insulin of Structure 10.

(A) Synthesis of Partially Protected and Carboxyl Group Activated Insulin Gly(A21)-Chain of Structure 6.

3.0 g (1.0 mmol) of H-Gly-O-CTC resin (commercially available, Product of CBL-Patras) was elongated to the resin-bound protected Gly(A21)-chain using Fmoc-amino acids (Products of CBL-Patras) and DIC/HOBt for the activation of the amino acids except of the Gly(A1) residue which was introduced using Boc-Gly-OH. The resin was then washed 4× with NMP and 6× with DCM and then the protected peptide was cleaved from the resin and oxidized simultaneously by washing 8× with 1%-TFA in DCM containing 20.0 mmol of iodine. The filtrates from the 1% TFA washings were dropped into a 3% $Na_2S_2O_3$ solution, the DCM layer was washed with the $Na_2S_2O_3$ solution and water, concentrated in the RE and the protected peptide was then precipitated with the addition of DEE, washed with DEE and dried in vacuum to constant weight. Yield 3.04 g (90.0%).

H-Gly-O-CTC-resin

↓ solid-phase synthesis

Boc-Gly-Ile-Val-Glu(tBu)-Gln(Trt)-Cys(Trt)-Cys(Trt)-Thr(tBu)-Ser(tBu)-Ile-Cys(Trt)-Ser(tBu)-Leu-Tyr(tBu)-Gln(Trt)-Leu-Glu(tBu)-Asn(Trt)-Tyr(tBu)-Cys(Trt)-Gly-O-CTC-resin (4)

↓ 1%-TFA/$I_2$

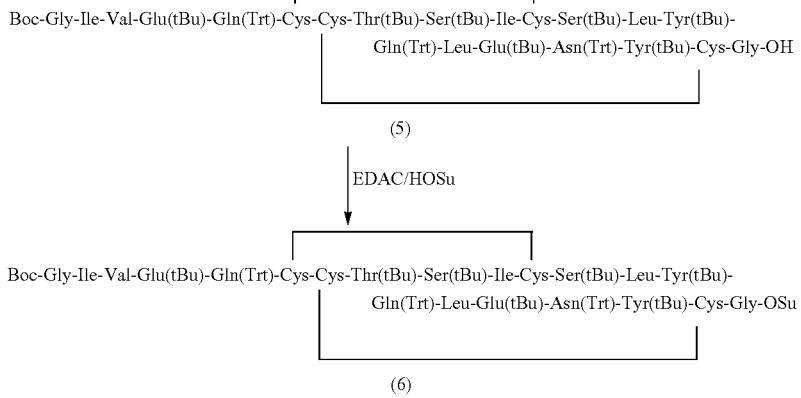

(5)

↓ EDAC/HOSu

Boc-Gly-Ile-Val-Glu(tBu)-Gln(Trt)-Cys-Cys-Thr(tBu)-Ser(tBu)-Ile-Cys-Ser(tBu)-Leu-Tyr(tBu)-Gln(Trt)-Leu-Glu(tBu)-Asn(Trt)-Tyr(tBu)-Cys-Gly-OSu (6)

(B) Solid-Phase Synthesis of Selectively at the Lys[29] Deprotected B(Arg31), B(Arg32) Human Insulin B Chain of Structure 8.

4.0 g (1.0 mmol) of H-Arg(Pbf)-O-CTC resin (commercially available from CBL-Patras), was elongated to the resin-bound protected Arg(B31), Arg(B32)-chain using Fmoc-amino acids and DIC/HOBt for the activation of the amino acids except of the Phe(B1) residue which was introduced using Boc-Phe-OH. The resin was then washed 4× with NMP and 6× with DCM and then the protected peptide was cleaved from the resin washing 8× with 1%-TFA in DCM. The filtrates from the 1% TFA washings were dropped into a water solution of 1%-pyridine, the DCM layer was washed with water, concentrated in the RE and the protected peptide was then precipitated with the addition of DEE, washed with DEE and dried in vacuum to constant weight. Yield 5.61 g (90.2%).

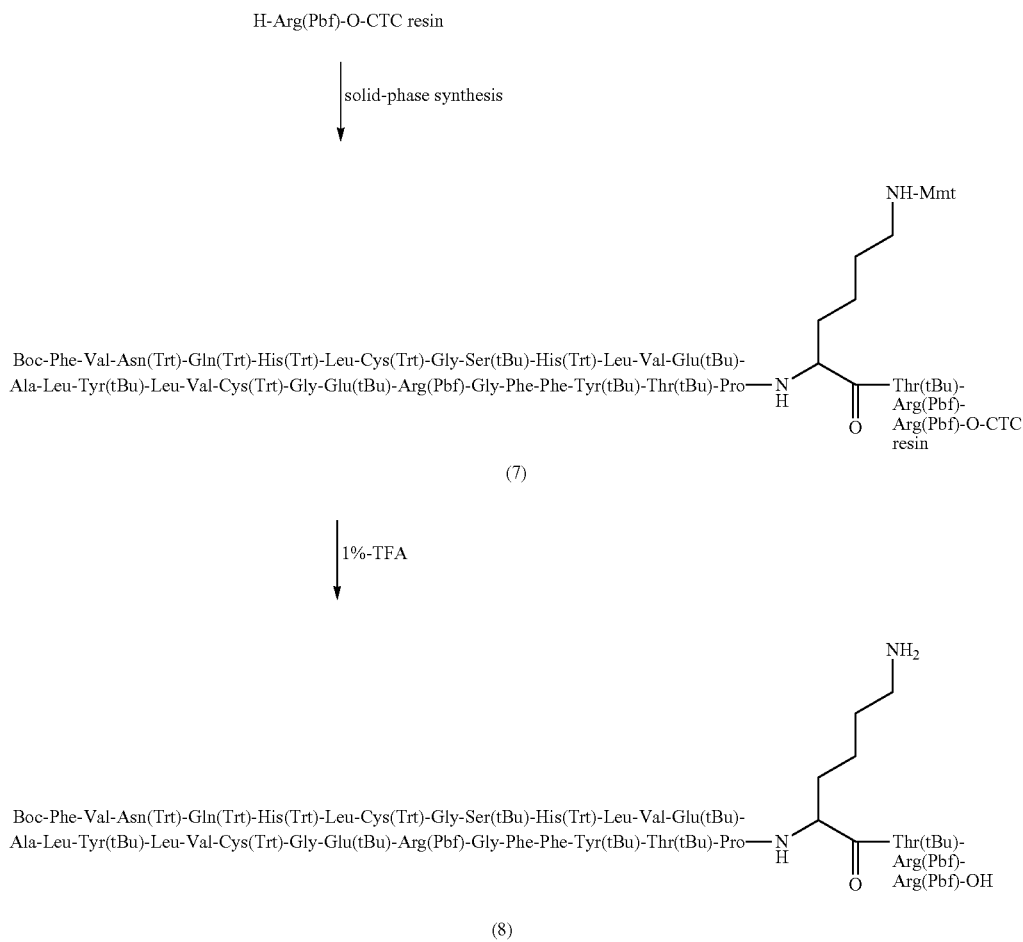

(C) Condensation in Solution—Synthesis of Single Chain Insulin Nr. 10

To a solution of 427.1 mg (0.1 mmol) protected A-chain Nr. 6 in 10.0 ml DMF 0.12 (0.1 mmol) HOSu and 0.17 g (0.1 mmol) EDAC were added and the mixture was stirred for 20 min at RT. Then 621.9 mg (0.1 mmol) of the selectively at the B-chain deprotected insulin B-chain Nr. 8 were added and the resulting mixture was stirred for additional 6 h at RT. The resulting solution was then dropped to 100 ml ice cold water and the resulting solid was filtered, washed with water and dried in vacuum. Then the solid was dissolved in 30 ml of a precooled at 0° C. mixture of TFA/DTT/water (94:3:3) and stirred for 1 h and then the mixture was warmed to RT and stirred for additional 3 h at RT. The mixture was then concentrated in vacuum on a RE to ca 5 ml and 100 ml of ice cold DEE were added. The precipitated solid was filtered and washed with DEE and dried in vacuum to constant weight. Then the crude insulin was dissolved in 20% DMSO in a $Na_2HPO_4$ solution at pH=7.8 and stirred for additional 48 h at RT. The obtained solution was then acidified and loaded to a C18 Chromasil column and purified by HPLC. The fractions which contained the main product were collected and lyophilized. Yield: 62.3 mg net peptide (10.7%).

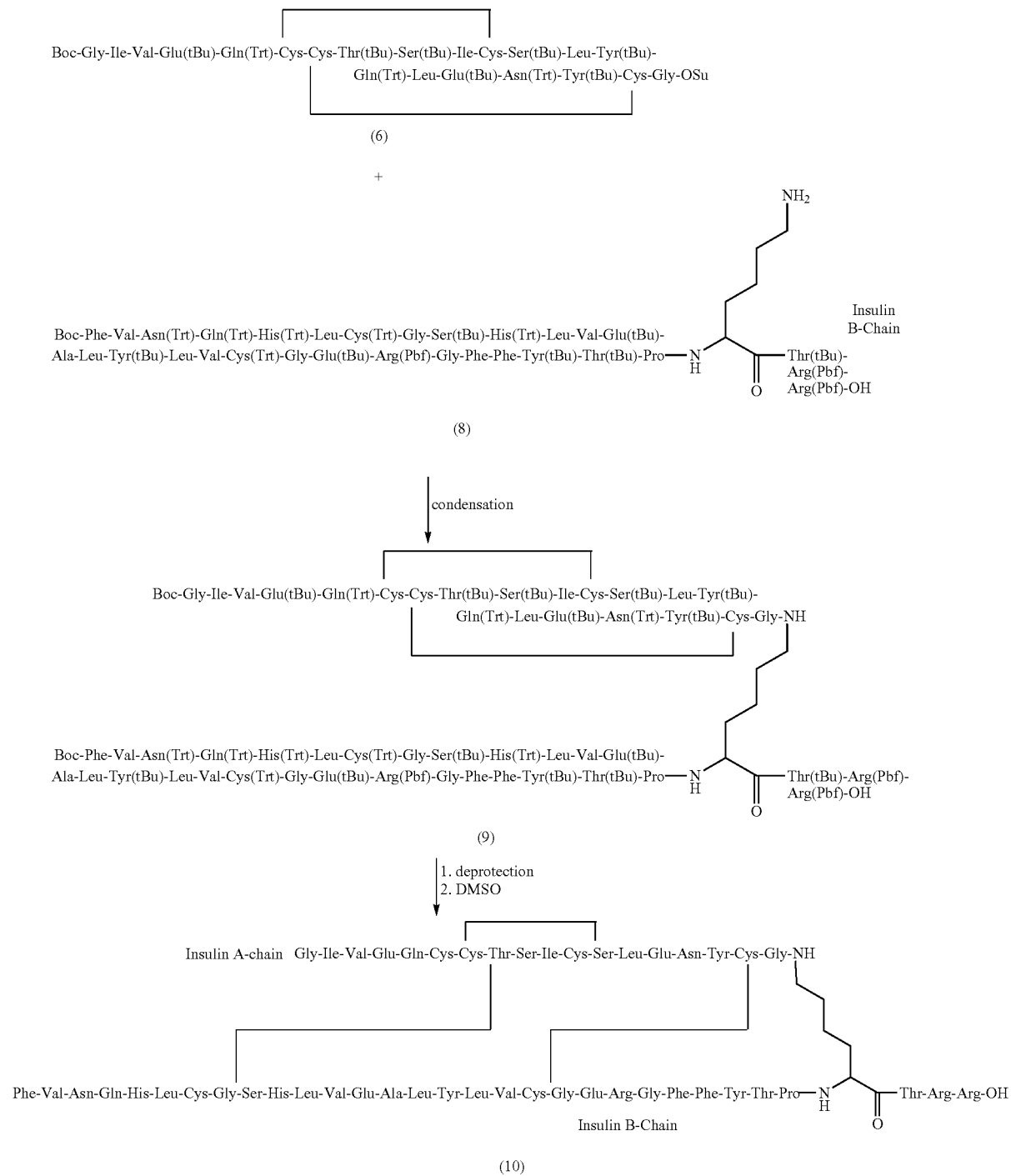

Example 2

Synthesis of Single Chain Insulin with Structure 15.

(A) Synthesis of Protected, Carboxyl Group Activated and Oxidized Asp[21] Insulin A-Chain of Structure 11.

4.0 g (1.0 mmol) of H-Asp(CTC resin)-O$^t$Bu (commercially available from CBL-Patras) was elongated to the resin-bound protected Asp(A21)-chain using Fmoc-amino acids (Products of CBL-Patras) and DIC/HOBt for the activation of the amino acids except of the Gly(A1) residue which was introduced using Boc-Gly-OH. The resin was then washed 4× with NMP and 6× with DCM and then the protected peptide was cleaved from the resin and oxidized simultaneously by washing 8× with 1%-TFA in DCM which contained 20.0 mmol of iodine. The filtrates from the 1% TFA washings were dropped into a 3% $Na_2S_2O_3$ solution, the DCM layer was washed with the $Na_2S_2O_3$ solution and water, concentrated in the RE and the protected peptide was then precipitated with the addition of DEE, washed with DEE and dried in vacuum to constant weight. Yield 2.97 g (87.5%).

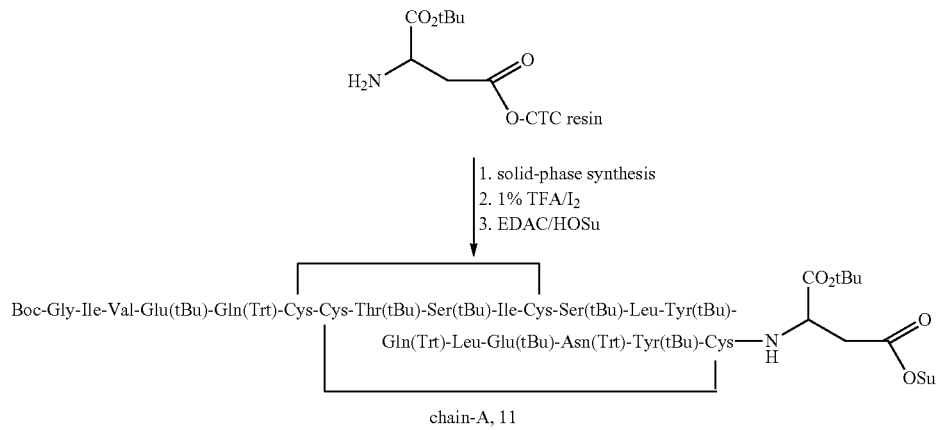

chain-A, 11

(B) Synthesis of Selectively at the Lys[29] Side Chain Deprotected des-Thr[30] Human Insulin of Structure 12.

3.2 g (1.0 mmol) of H-Lys(MMT resin)-OTrt (produced by reacting Fmoc-Lys-OH with MMt-chloride resin and DIPEA in DCM, followed by the esterification of the resin-bound Fmoc-Lys-OH obtained with Trt-chloride) was elongated to the resin-bound protected desThr(B30) human insulin B-chain using Fmoc-amino acids (Products of CBL-Patras) and DIC/HOBt for the activation of the amino acids except of the Phe(B1) residue which was introduced using Boc-Phe-OH. The resin was then washed 4× with NMP and 6× with DCM and then the protected peptide was cleaved from the resin by washing 8× with 1%-TFA in DCM. The filtrates from the 1% TFA washings were dropped into a water solution of 1%-pyridine, the DCM layer was washed with water, concentrated in the RE and the protected peptide was then precipitated with the addition of DEE, washed with DEE and dried in vacuum to constant weight. Yield 4.93 g (94.1%).

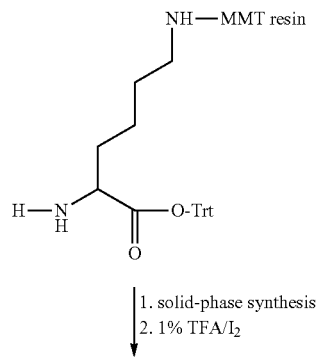

Boc-Phe-Val-Asn(Trt)-Gln(Trt)-His(Trt)-Leu-Cys(Trt)-Gly-Ser(tBu)-His(Trt)-Leu-Val-Glu(tBu)-
Ala-Leu-Tyr(tBu)-Leu-Val-Cys(Trt)-Gly-Glu(tBu)-Arg(Pbf)-Gly-Phe-Phe-Tyr(tBu)-Thr(tBu)-Pro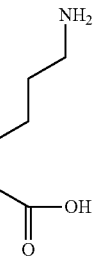

chain-B, 12

15

(C) Condensation of the Partially Protected Insulin Chains A and B in Solution

To a solution of 339.6 mg (0.1 mmol) protected A-chain Nr. 11 in 10.0 ml DMF 0.12 (0.1 mmol) HOSu and 0.17 g (0.1 mmol) EDAC were added and the mixture was stirred for 20 min at RT. Then 524.5 mg (0.1 mmol) of the selectively at the B-chain deprotected insulin B-chain Nr. 12 were added and the resulting mixture was stirred for additional 6 h at RT. The resulting solution was then dropped to 100 ml ice cold water and the resulting solid was filtered, washed with water and dried in vacuum. Then the solid was dissolved in 30 ml of a precooled at 0° C. mixture of TFA/DTT/water (94:3:3) and stirred for 1 h and then the mixture was warmed to RT and stirred for additional 3 h at RT. The mixture was then concentrated in vacuum on a RE to ca 5 ml and 100 ml of ice cold DEE were added. The precipitated solid was filtered and washed with DEE and dried in vacuum to constant weight. Then the crude insulin was dissolved in 20% DMSO in a $Na_2HPO_4$ solution at pH=7.8 and stirred for additional 48 h at RT. The obtained solution was then acidified and loaded to a C18 Chromasil column and purified by HPLC. The fractions which contained the main product were collected and lyophilized. Yield: 78.9 mg net peptide (14.5%).

A + B

| condensation

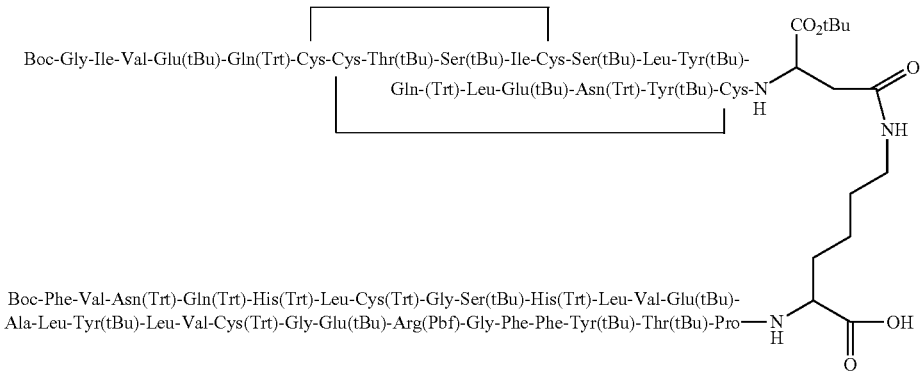

(13)

| deprotection

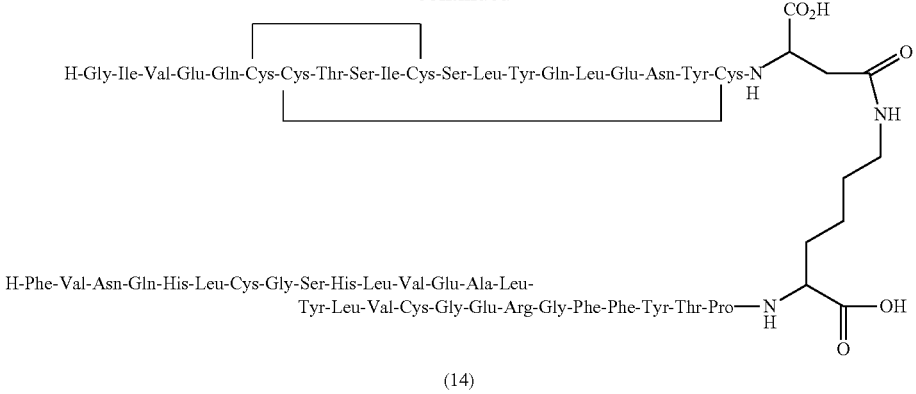

(14)

↓ DMSO/DTT

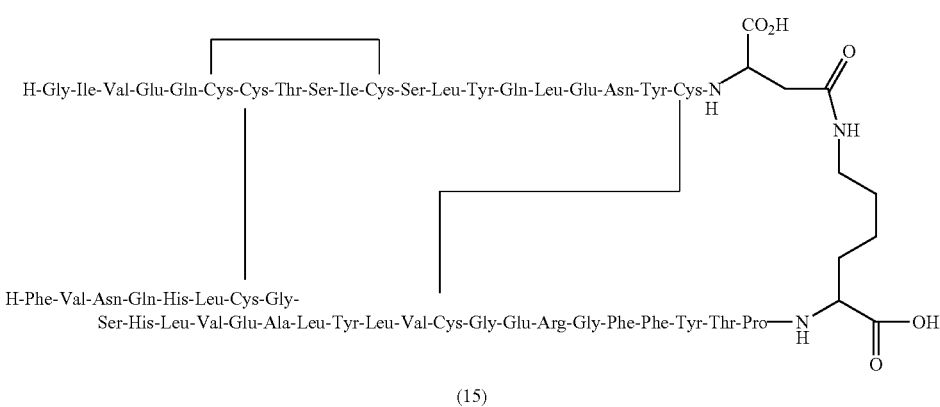

(15)

Example 3

Synthesis of Single Chain Insulin with Structure 19.

(A) Synthesis of Protected Insulin Chain-A with Structure 17.

4.13 g (10.0 mmol) of 6-Fmoc-amino(ethylthio)hexanoic acid, obtained by procedures well known in the art from Fmoc-cysteamine and 6-bromohexanoic acid, were dissolved in 200 ml DCM and then 20.0 g (1.6 mmol/g) CTC-chloride resin and 7.75 g (60 mmol) DIPEA were added and the mixture was shacked for 2 h at RT. Then 10.0 ml MeOH were added and the mixture was shacked for an additional h. The resin was filtered and washed 3× DCM/ DIPEA/MeOH, 6× DCM. The obtained resin bound amino acid was then chain elongated with sequential couplings of Fmoc-amino acids and DIC/HOBt for their activation to the resin-bound protected peptide 16. The resin 16 was then washed 4× with NMP and 6× with DCM and then the protected peptide was cleaved from the resin and oxidized simultaneously by washing 8× with 1%-TFA in DCM which contained 200.0 mmol of iodine. The filtrates from the 1% TFA washings were dropped into a water solution of 1%-pyridine, the DCM layer was washed with water, concentrated in the RE and the protected peptide was then precipitated with the addition of DEE, washed with DEE and dried in vacuum to constant weight. Yield 34.7 g (90.8%).

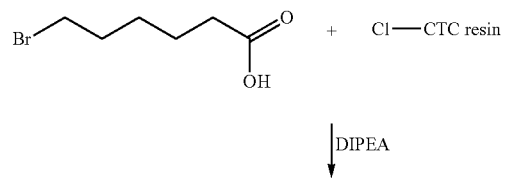

↓ DIPEA

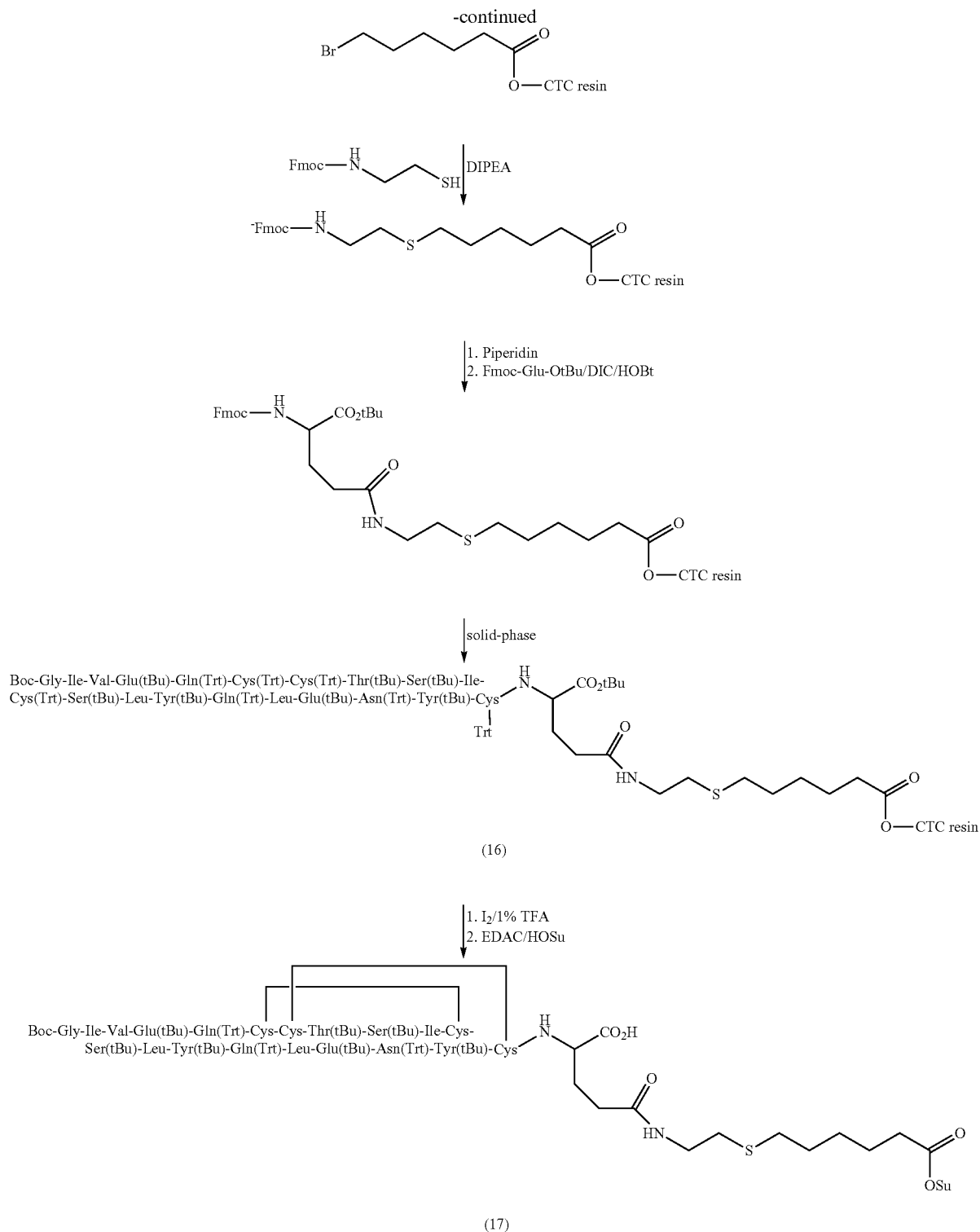

(B) Condensation in Solution of the Partially Protected and Modified Insulin Chain A of Structure 17 with the Partially Protected Chain B of des Thr(B30) Insulin of Structure 12.

To a solution of 382.3 mg (0.1 mmol) protected A-chain Nr. 17 in 10.0 ml DMF 0.12 (0.1 mmol) HOSu and 0.17 g (0.1 mmol) EDAC were added and the mixture was stirred for 20 min at RT. Then 524.5 mg (0.1 mmol) of the selectively at the side chain of Lys(B 29) deprotected des(B30) insulin B-chain Nr. 12 were added and the resulting mixture was stirred for additional 6 h at RT. The resulting solution was then dropped to 100 ml ice cold water and the resulting solid was filtered, washed with water and dried in vacuum. Then the solid was dissolved in 30 ml of a precooled at 0° C. mixture of TFA/DTT/water (94:3:3) and stirred for 1 h and then the mixture was warmed to RT and stirred for additional 3 h at RT. The mixture was then concentrated in vacuum on a RE to ca 5 ml and 100 ml of ice cold DEE were added. The precipitated solid was filtered and washed with DEE and dried in vacuum to constant weight. Then the crude insulin was dissolved in 20% DMSO in a $Na_2HPO_4$ solution at pH=7.8 and stirred for additional 48 h at RT. The obtained solution was then acidified and loaded to a C18 Chromasil column and purified by HPLC. The fractions which contained the main product were collected and lyophilized. Yield: 127.4 mg net peptide (22.8%).

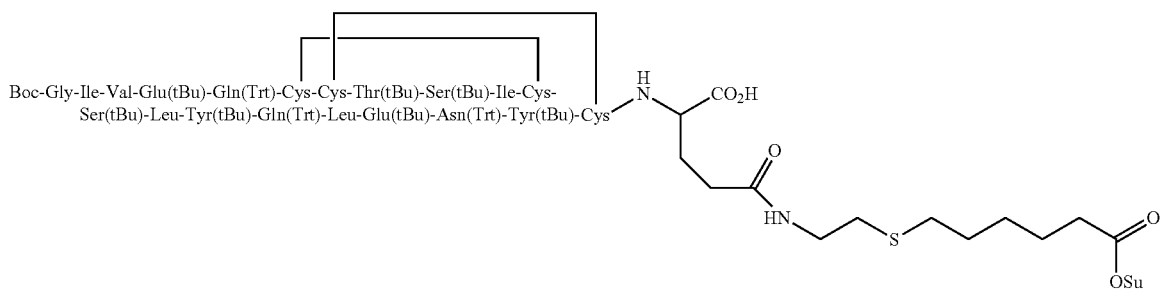

(17)

+

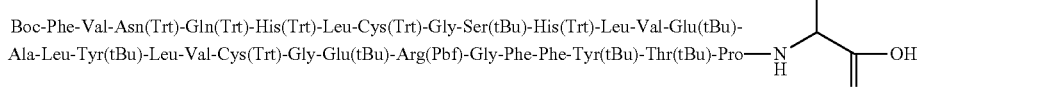

(12)

↓

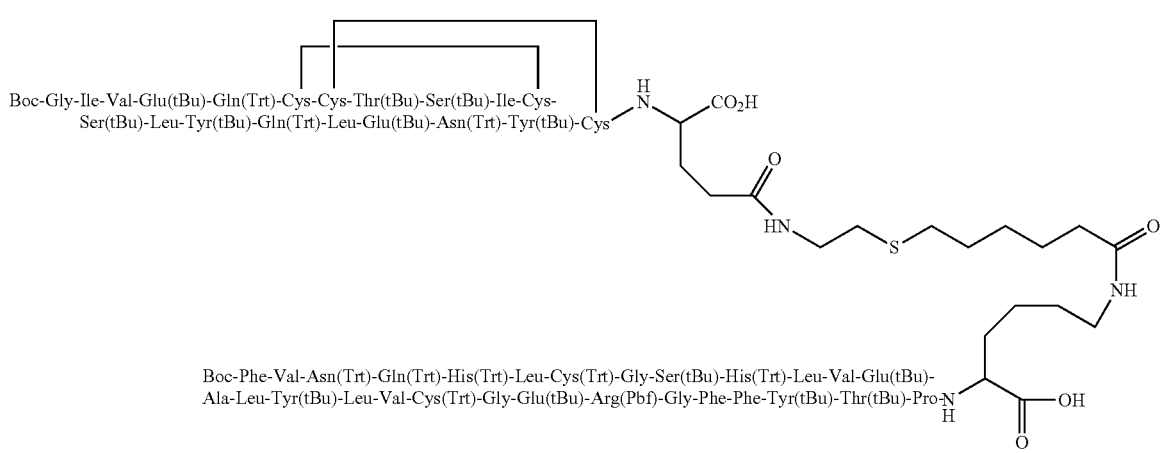

(18)

1. TFA
2. DTT/DMSO

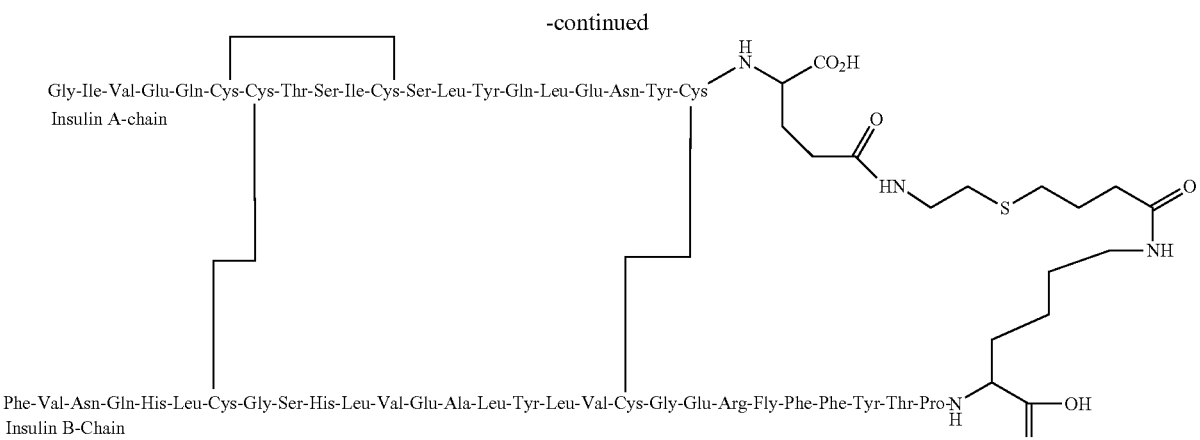

(19)

Example 4

Synthesis of Single Chain Insulin of Structure 23.

Solid-Phase Synthesis of Single Chain Insulin Glu(A21), des Thr(B30) where the Insulin Chains are Connected Through the Side Chains of Glu(A21) and Lys(B29) and the Oligoethylen Glycol Modifier.

The synthesis was started with the solid phase synthesis of the B-chain on 4-methyl-benzhydryl(diphenylmethyl) resin. After the completion of the synthesis the side chain Lys (B29) Mmt function was removed by the treatment of the resin with DCM/TFE/AcOH (7:2:1) for 3 h at RT to provide the partially protected resin-bound peptide of structure 21. Then on the Lys side chain two groups of 2-(2-(2-aminoethoxy)ethoxy)acetic acid were introduced using the corresponding Fmoc-derivatives followed by the coupling with Fmoc-Glu-OtBu. On the Nα-function of the Glu(A21) the rest of the A chain was assembled using Fmoc-amino acids. After the completion of the synthesis the resin-bound peptide was treated with 1% $I_2$ in DCM/TFE (9:1) in order to build the disulfide bonds. The resin was then washed with DCM and treated with TFA/DTT/$H_2O$ (94:3:3) for 15 min at 0° C. and filtered. The resin was then washed 3× with the TFA solution and the combined filtrates were left at 0° C. for additional 3 h. The solution was concentrated on a RE and the remaining oil was dropped to ice cold DEE. The precipitated material was filtered, washed with DEE and dried in vacuum. Then the crude insulin was dissolved in 20% DMSO in a $Na_2HPO_4$ solution at pH=7.8 and stirred for additional 48 h at RT. The obtained solution was then acidified and loaded to a C18 Chromasil column and purified by HPLC. The fractions which contained the main product 23 were collected and lyophilized. Yield: 82.4 mg net peptide (14.29%).

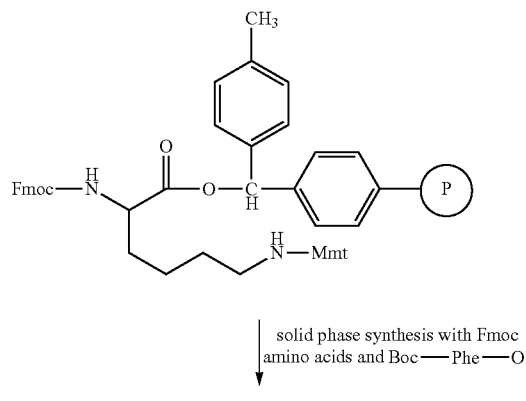

solid phase synthesis with Fmoc amino acids and Boc—Phe—OH

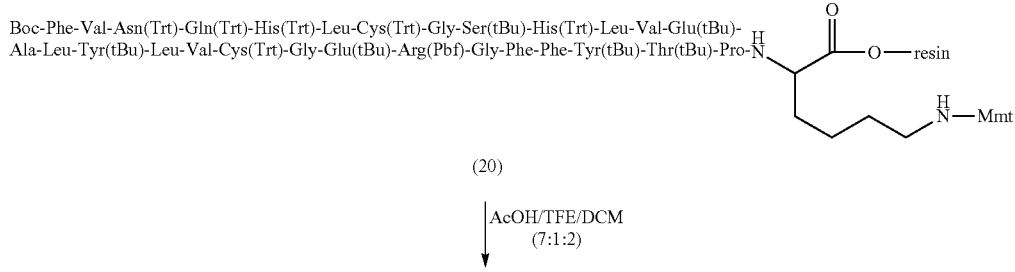

(20)

AcOH/TFE/DCM
(7:1:2)

-continued

Boc-Phe-Val-Asn(Trt)-Gln(Trt)-His(Trt)-Leu-Cys(Trt)-Gly-Ser(tBu)-His(Trt)-Leu-Val-Glu(tBu)-Ala-Leu-Tyr(tBu)-Leu-Val-Cys(Trt)-Gly-Glu(tBu)-Arg(Pbf)-Gly-Phe-Phe-Tyr(tBu)-Thr(tBu)-Pro-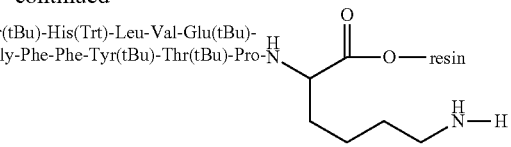

(21)

1. Fmoc-NH-CH₂CH₂-O-CH₂CH₂-O-CH₂-CO₂H/DIC/HOBt(2 cycles)

2. solid-phase synthesis with Fmoc-amino acid and Boc—Gly—OH

Boc-Phe-Val-Asn(Trt)-Gln(Trt)-His(Trt)-Leu-Cys(Trt)-Gly-Ser(tBu)-His(Trt)-Leu-Val-Glu(tBu)-Ala-Leu-Tyr(tBu)-Leu-Val-Cys(Trt)-Gly-Glu(tBu)-Arg(Pbf)-Gly-Phe-Phe-Tyr(tBu)-Thr(tBu)-Pro-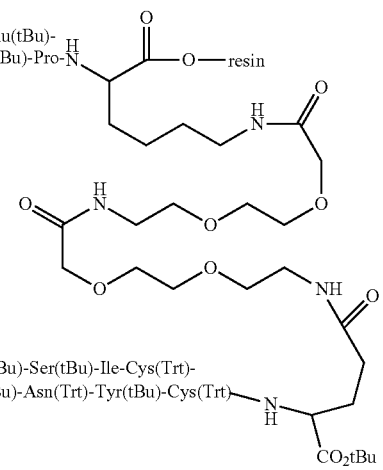

Boc-Gly-Ile-Val-Glu(tBu)-Gln(Trt)-Cys(Trt)-Cys(Trt)-Thr(tBu)-Ser(tBu)-Ile-Cys(Trt)-Ser(tBu)-Leu-Tyr(tBu)-Gln(Trt)-Leu-Glu(tBu)-Asn(Trt)-Tyr(tBu)-Cys(Trt)-

(22)

1. I₂
2. TFA
3. DTT/DMSO

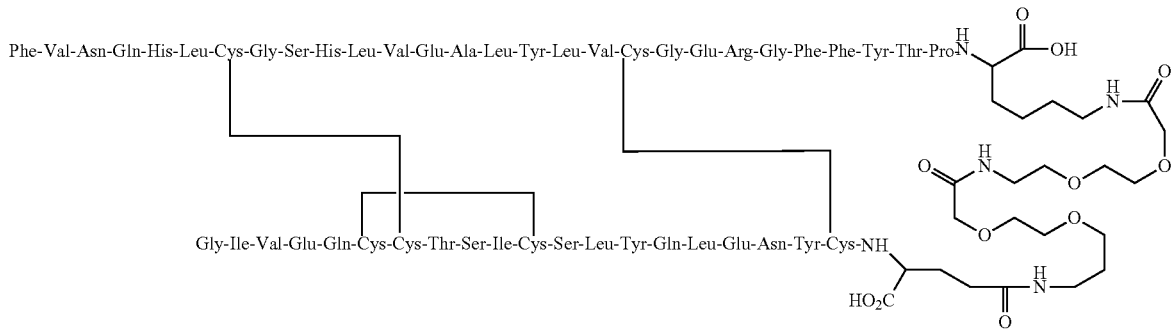

(23)

Example 5

Synthesis of the Single Chain Insulin Synthesis of Structure 24 on 2-chlorotrityl Resin The synthesis was started from 1.00 mmol H-Thr(tBu)-O-CTC resin and was performed as described in Example 3 with the exception that instead of Fmoc-Lys(Mmt)-OH for the introduction of Lys(B29) Fmoc-Lys(Dde)-OH was used and the selective removal of Dde was performed as usual with 2%-hydrazine in NMP. Yield: 94.3 mg (15.4%).

(24)

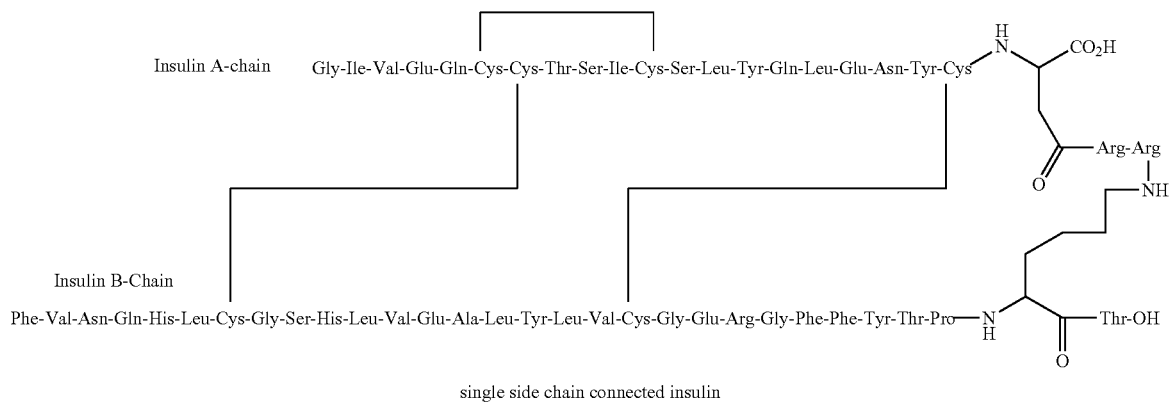

single side chain connected insulin

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

The invention claimed is:
1. A single chain insulin analogue comprising:
 (A) the A-chain of human or animal insulin, or an analogue or derivative thereof;
 (B) the B-chain of human or animal insulin, or an analogue or derivative thereof;
 (C) one or more disulfide bonds between said A-chain and said B-chain; and
 (D) a further covalent link, L, between:
  (i) the carboxyl terminal amino acid of said A-chain or analogue or derivative thereof, or a side chain carboxyl group of an amino diacid present in the C-terminal part of said A-chain, wherein the C-terminal part refers to the last 10 amino acids of the A-chain including possible peptide extensions; and
  (ii) the side chain of the lysine residue in position 29 of said B-chain or analogue or derivative thereof.
2. The single chain insulin analogue of claim 1, wherein the further covalent link, L, is a direct bond.
3. The single chain insulin analogue of claim 2, wherein the further covalent link L is a direct bond between the side chain of an aspartic acid residue or of an glutamic acid residue at the C-terminal amino acid of the A-chain and the side chain amino function of a Lys residue in the B-chain.
4. The single chain insulin analogue of claim 1, wherein the further covalent link, L, is a group comprising:
 (i) at least one group X; and/or
 (ii) at least one group Y; and/or
 (iii) at least one group Z;
 wherein:
  X is a group of formula 1a or 1b

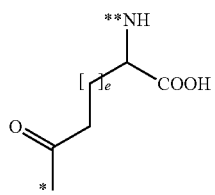

1a

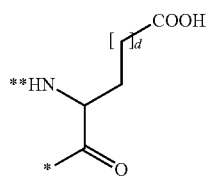

1b wherein d and e are each independently an integer selected from 0 to 10, and * and ** denote the points of attachment to the respective adjacent groups;
Y is a group selected from the following:

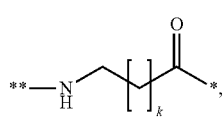

4

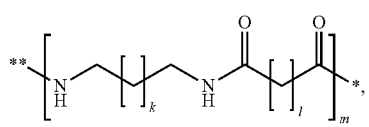

5

-continued
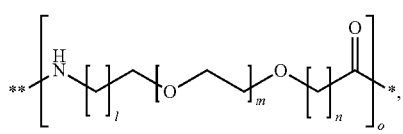
6
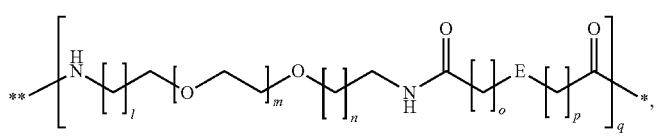
7
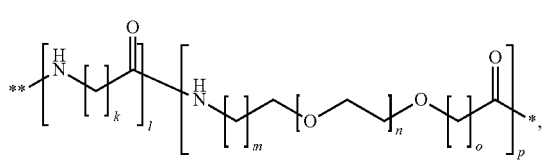
8
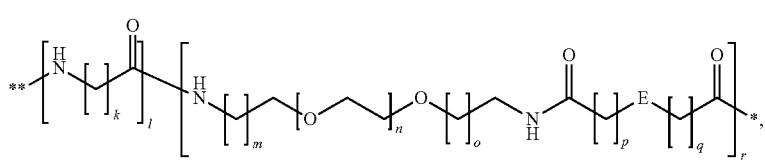
9
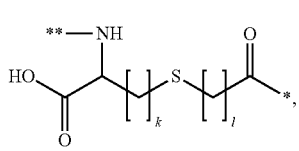
10
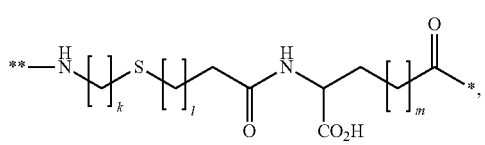
11
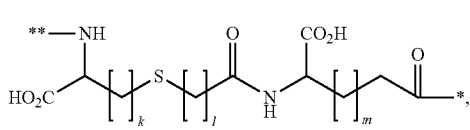
12
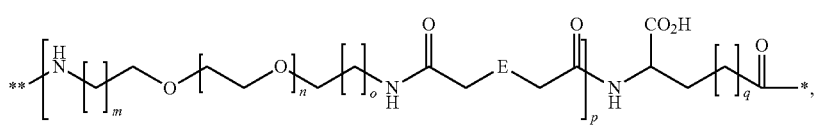
13
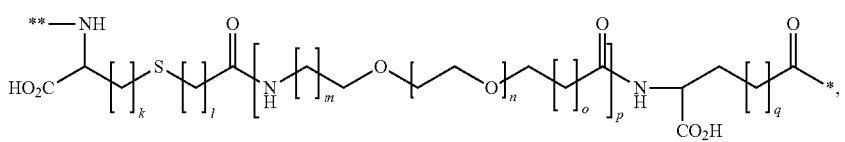
14
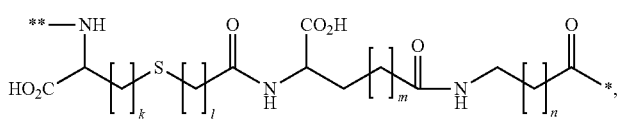
15
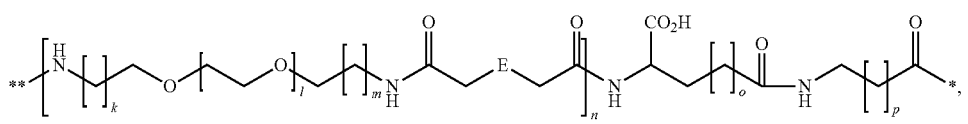
16

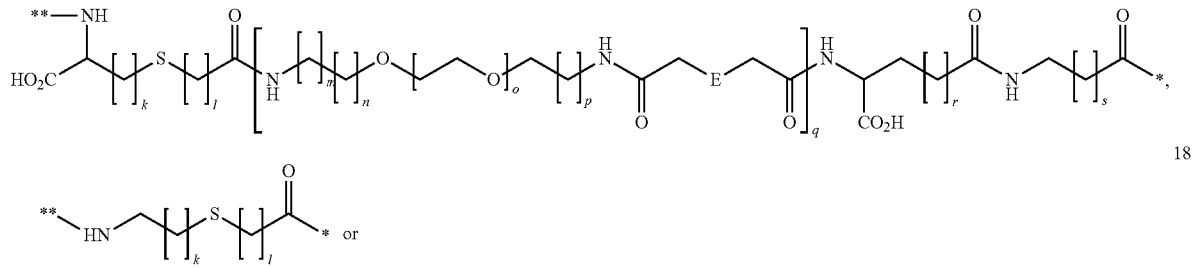

where * and ** denote the points of attachment to the respective adjacent groups;
k, l, m, n, o, p q, r, and s are each independently an integer selected from 0 to 18; and
E is absent or is selected from $CH_2$, O, S and NR, where R is H, alkyl or aralkyl; and
Z is a natural or unnatural amino acid.

5. The single chain insulin analogue of claim 4, wherein L is selected from the following groups:
(i) —(X)a-(Y)b-(Z)x-,
(ii) —(Y)b-(X)a-(Z)c-,
(iii) —(Y)$_b$—(Z)c-(X)a-,
(iv) —(X)$_a$—(Z)$_c$—(Y)b-,
(v) —(Z)c-(X)a-(Y)b-, and
(vi) —(Z)c-(Y)b-(X)a-
where a, b and c are each independently an integer selected from 0 to 5.

6. The single chain insulin analogue of claim 5, wherein a, b and c are each independently 0, 1 or 2.

7. The single chain insulin analogue of claim 5, wherein L is selected from:
(i) —(X)$_a$—(Y)$_b$—(Z)$_c$— where a is 1, and b and c are both 0;
(ii) —(X)$_a$—(Y)$_b$—(Z)$_c$— where a and b are 1, and c is 0;
(iii) —(X)$_a$—(Y)$_b$—(Z)$_c$— where a is 1, b is 2, and c is 0;
(iv) —(X)$_a$—(Y)$_b$—(Z)$_c$— where a is 1, b is 0, and c is 2; and
(v) —(X)$_a$—(Y)$_b$—(Z)$_c$— where a is 0, b is 0, and c is 1.

8. The single chain insulin analogue of claim 4, wherein X is a group of formula 1a.

9. The single chain insulin analogue of claim 4, wherein Y is a group of formula 6 as defined in claim 4.

10. The single chain insulin analogue of claim 9, wherein Y is a group of formula 6a or 6b

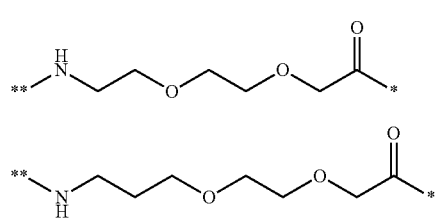

where * and ** denote the points of attachment to the respective adjacent groups.

11. The single chain insulin analogue of claim 1, wherein Y is a group of formula 18 as defined in claim 4.

12. The single chain insulin analogue of claim 11, wherein Y is a group of formula 18a, where I is 1, 2, 3, 4 or 5

18a where * and ** denote the points of attachment to the respective adjacent groups.

13. The single chain insulin analogue of claim 1, wherein the A-chain comprises amino acids 1 to 21 or 1 to 20 of human insulin counting from the N-terminal end of the A chain.

14. The single chain insulin analogue of claim 1, wherein the B-chain comprises amino acids 1 to 29 of human insulin counting from the N-terminal end of the B chain.

15. The single chain insulin analogue of claim 14, wherein the B-chain of insulin further comprises 1, 2, or 3 additional natural or unnatural amino acids at the C-terminal end.

16. The single chain insulin analogue of claim 1, which comprises one or more of:
(i) an intermolecular disulfide bond between the cysteine in position 7 of the insulin A-chain and the cysteine in position 7 of the insulin B-chain;
(ii) an intermolecular disulfide bond between the cysteine in position 20 of the insulin A-chain and the cysteine in position 19 of the insulin B-chain;
(iii) an intramolecular disulfide bond between the cysteine in position 6 and the cysteine in position 11 of the insulin A-chain.

17. The single chain insulin analogue of claim 1, which is of formula (I), (I)

Insulin A-chain

H-Gly-Ile-Val-Glu-Gln-Cys-Cys-Thr-Ser-Ile-Cys-Ser-Leu-Tyr-Gln-Leu-Glu-Asn-Tyr-Cys—L

Phe-Val-Asn-Gln-His-Leu-Cys-Gly-Ser-His-Leu-Val-Glu-Ala-Leu-Tyr-Leu-Val-Cys-Gly-Glu-Arg-Gly-Phe-Phe-Tyr-Thr-Pro-Lys-(Aaa$_1$)$_r$-R

Insulin B-chain

B29 wherein:
L is as defined in claim 1;
each Aaa$_1$ is independently a natural or unnatural amino acid;
f is an integer selected from 0 to 3;
R is OH or NH$_2$.

18. The single chain insulin analogue of claim 17, wherein R is OH, and each Aaa$_1$ is independently a natural amino acid, more preferably selected from Arg and Thr.

19. The single chain insulin analogue of claim 1, which is selected from the following:

[1]
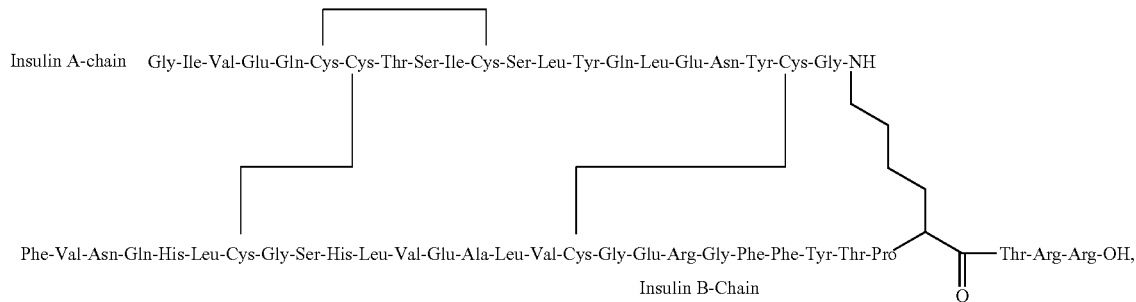

[2]
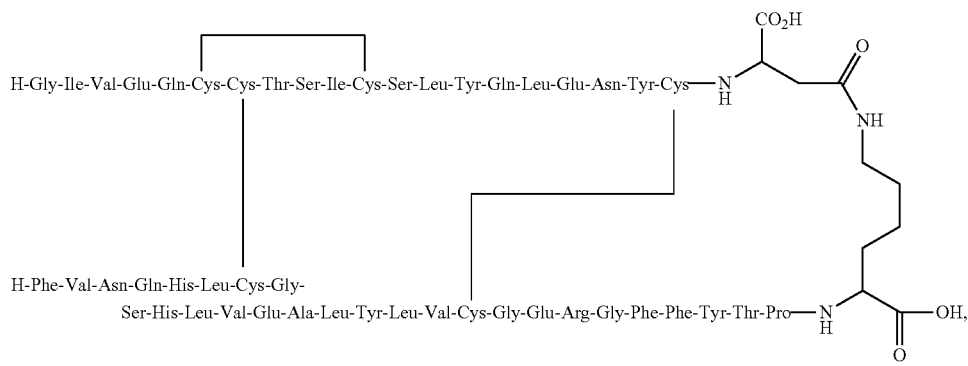

[3]
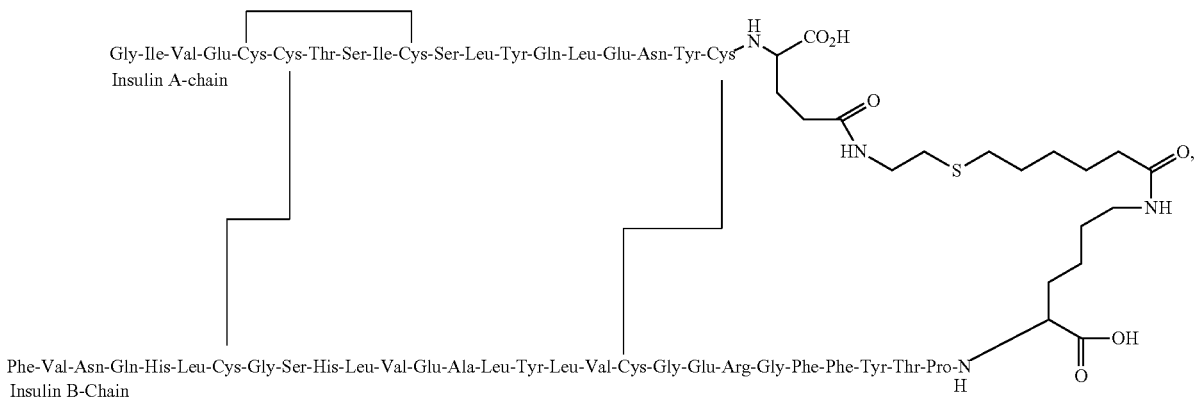

[4]
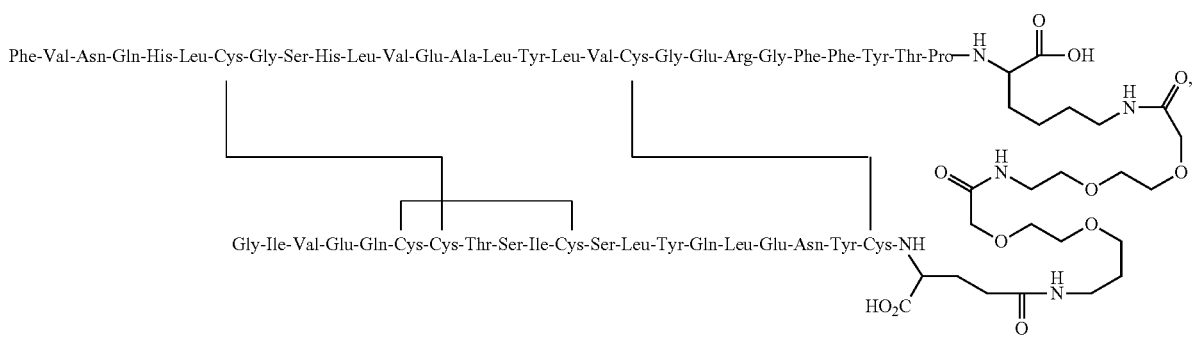

-continued

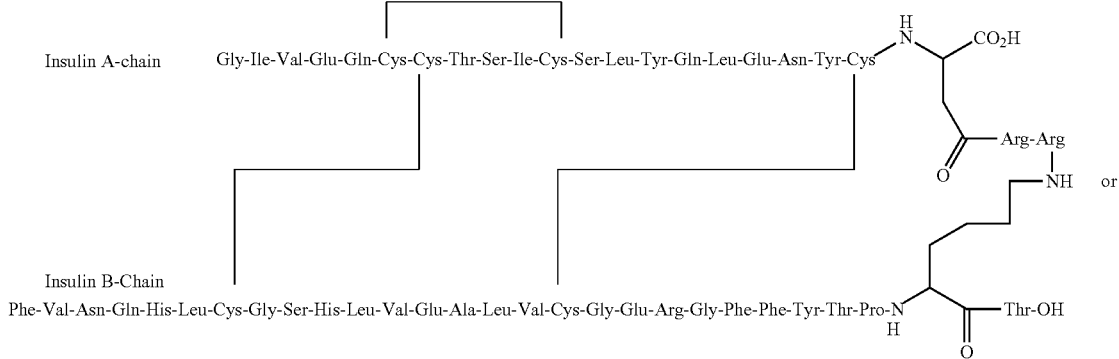

[5]

20. A pharmaceutical composition comprising the single chain insulin analogue of claim 1, and a pharmaceutically acceptable diluent, excipient or carrier.

21. A method of treating diabetes, or treating or preventing hyperglycemia, in a subject in need thereof, said method comprising administering a therapeutically effective amount of the single chain insulin analogue of claim 1.

* * * * *